United States Patent
Argade et al.

(10) Patent No.: US 7,585,883 B2
(45) Date of Patent: Sep. 8, 2009

(54) SUBSTITUTED PYRIDINES AND THEIR USES

(75) Inventors: Ankush Argade, Foster City, CA (US); David Carroll, San Francisco, CA (US); Alexander B. Rossi, Reedsport, OR (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 175 days.

(21) Appl. No.: 11/264,629

(22) Filed: Oct. 31, 2005

(65) Prior Publication Data

US 2006/0178407 A1 Aug. 10, 2006

Related U.S. Application Data

(60) Provisional application No. 60/623,652, filed on Oct. 29, 2004.

(51) Int. Cl.
*A61K 31/4418* (2006.01)
*A61K 31/4425* (2006.01)

(52) U.S. Cl. .............. 514/349; 514/347; 514/348; 514/350; 514/351; 546/294; 546/296; 546/297; 546/298; 546/300; 546/301; 546/302; 546/303

(58) Field of Classification Search .............. 546/288, 546/294, 295, 296, 297, 298, 300, 301, 302, 546/303; 514/344, 347, 348, 349, 350, 351
See application file for complete search history.

(56) References Cited

U.S. PATENT DOCUMENTS

| 4,713,388 | A | * | 12/1987 | Ezer et al. ............. 514/346 |
| 5,246,948 | A | * | 9/1993 | Takatani et al. ........ 514/342 |
| 5,859,032 | A | | 1/1999 | Nishino et al. |
| 6,069,144 | A | * | 5/2000 | Wagner et al. ......... 514/301 |
| 2003/0229090 | A1 | | 12/2003 | Cywin et al. |

FOREIGN PATENT DOCUMENTS

WO  WO 00/56714  9/2000

OTHER PUBLICATIONS

Vippagunta et al., "Crystalline Solids", Advanced Drug Delivery Reviews 48 (2001) 3-26.*
Guillory, "Generation of, etc.," in Brittain ed, "Polymorphism in Pharmaceutical Solids", NY: Marcel Dekker, Inc. 1999, 183-226.*
Balant et al, "Metabolic Considerations, etc., Wolff ed," Burger's Medicinal Chemistry and Drug Discovery, fifth ed, vol. 1, 1995, 949-982.*
PCT International Search Report, Apr. 7, 2006.
Database Registry (Online), Oct. 25, 1999, *Chemical Abstracts Service*, Columbus, OH, US, XP002374182.

* cited by examiner

*Primary Examiner*—Patricia L Morris
(74) *Attorney, Agent, or Firm*—Swiss Tanner, P.C.

(57) ABSTRACT

The present invention is directed to substituted pyridines, methods for their preparation and methods for their use in the treatment and/or prevention of mast cell related conditions.

10 Claims, 3 Drawing Sheets

SUBSTITUTED PYRIDINES AND THEIR USES

1. CROSS-REFERENCE TO RELATED APPLICATION

Figure 1:
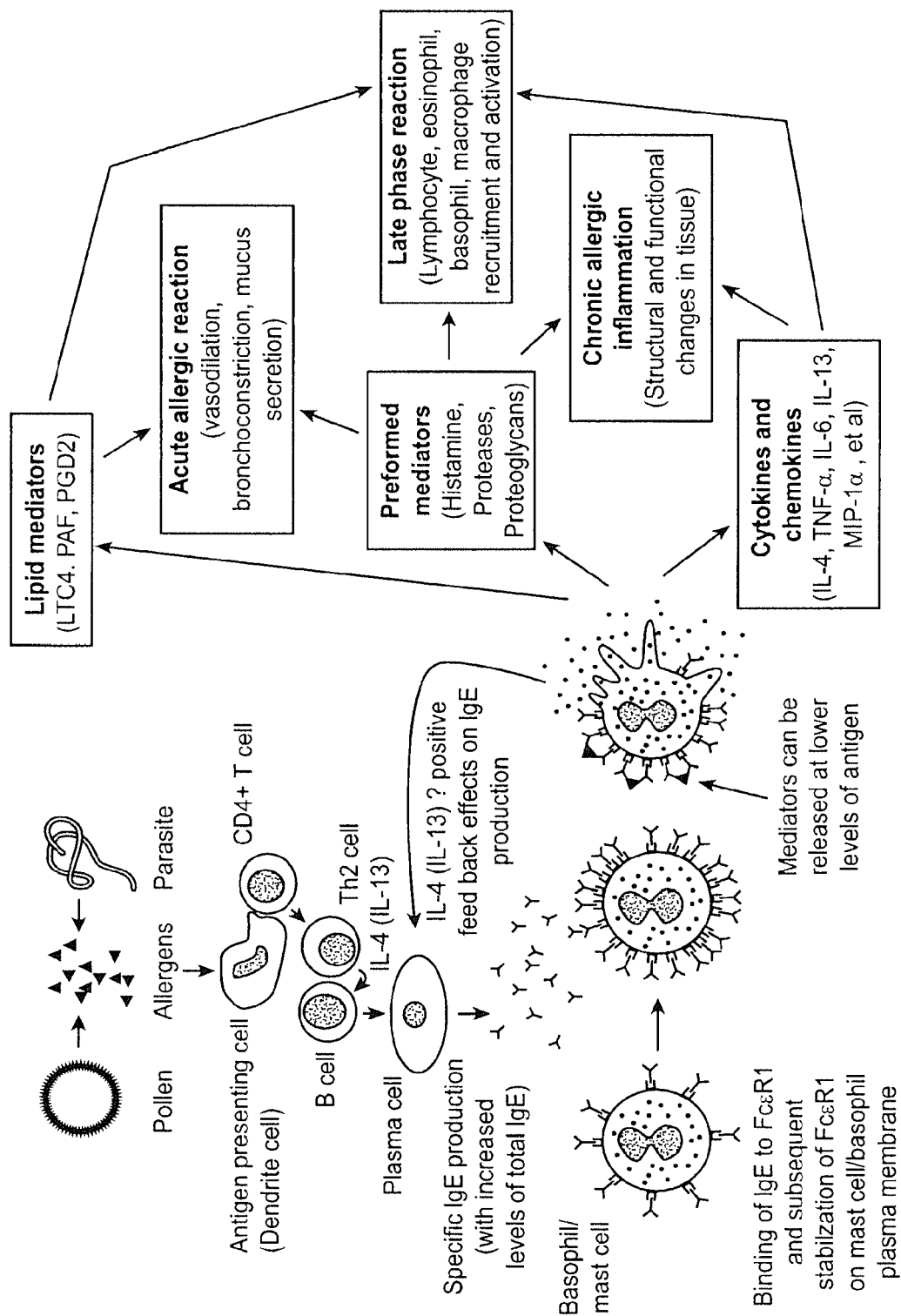

This application claims benefit under 35 U.S.C. § 119(e) to application Ser. No. 60/623,652 filed Oct. 29, 2004, the contents of which are incorporated herein by reference.

2. FIELD OF THE INVENTION

The present invention relates to substituted pyridine compounds, pharmaceutical compositions comprising the compounds, intermediates and synthetic methods of making the compounds and methods of using the compounds and compositions in a variety of contexts, such as in the treatment or prevention of autoimmune diseases and/or the symptoms associated therewith.

3. BACKGROUND OF THE INVENTION

Crosslinking of Fc receptors, such as the high affinity receptor for IgE (FcεRI) and/or the high affinity receptor for IgG (FcγRI) activates a signaling cascade in mast, basophil and other immune cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Additional mediators that are synthesized and released upon crosslinking Fc receptors include cytokines and nitric oxide.

The signaling cascade(s) activated by crosslinking Fc receptors such as FcεRI and/or FcγRI comprises an array of cellular proteins. Among the most important intracellular signal propagators are the tyrosine kinases. An important tyrosine kinase involved in the signal transduction pathways associated with crosslinking the FcεRI and/or FcγRI receptors, as well as other signal transduction cascades, is Syk kinase (see Valent et al., 2002, Intl. J. Hematol. 75(4):257-362 for review).

As the mediators released as a result of FcεRI and FcγRI receptor cross-linking are responsible for, or play important roles in, the manifestation of numerous adverse events, the availability of compounds capable of inhibiting the signaling cascade(s) responsible for their release would be highly desireable. Moreover, owing to the critical role that Syk kinase plays these and other receptor signaling cascade(s), the availability of compounds capable of inhibiting Syk kinase would also be highly desirable.

4. BRIEF SUMMARY OF THE INVENTION

In one aspect, the present invention provides novel substituted pyridine compounds that, as will be discussed in more detail below, have a myriad biological activities. The compounds generally comprise a substituted pyridine having the following structure (I):

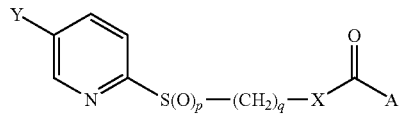

(I)

including pharmaceutically acceptable salts, hydrates, solvates and N-oxides thereof, wherein;

Y is —OH, —SH, —CN, —C(O)H, —NO$_2$, halo, fluoro, chloro, bromo, iodo, lower alkyl, substituted lower alkyl, lower heteroalkyl, substituted lower heteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, lower haloalkoxy, monohalomethoxy, dihalomethoxy, trihalomethoxy, trifluoromethoxy, amino, lower di- or monoalkylamino, substituted lower di- or monoalkylamino, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, thiocarbamoyl, substituted thiocarbamoyl, ureas, substituted ureas, thioureas, substituted thioureas, sulfamoyl, substituted sulfamoyl, cycloalkylimides, substituted cycloalkylimides, isoindole-1,3-diones, substituted isoindole-1,3-diones, phthalimide and substituted phthalimides;

p is 0, 1 or 2;

q is an integer between and including 1 through 6;

X is O, NH or NR$^3$;

R$^3$ is an alkyl, aryl, or progroup; and

A is an alkyl, substituted alkyl, alkoxy, substituted alkoxy, aryl, or substituted aryl.

In one embodiment, Y is an electron withdrawing group, i.e., —NO$_2$, a carbamate, a substituted carbamate, a urea, a substituted urea, a cycloalkylimide, a phthalimide, or a substituted phthalimide.

In another embodiment, the pyridine compound is not

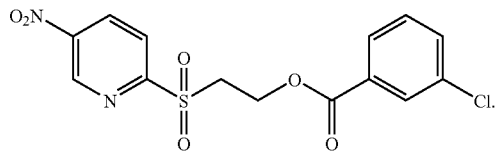

In another aspect, the present invention provides prodrugs of the pyridine compounds. Such prodrugs may be active in their prodrug form, or may be inactive until converted under physiological or other conditions of use to an active drug form. In the prodrugs of the invention, one or more functional groups of the pyridine compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs of the invention include special types of protecting groups, termed "progroups," masking one or more functional groups of the pyridine compounds that cleave under the conditions of use to yield an active pyridine drug compound. Functional groups within the pyridine compounds that may be masked with progroups for inclusion in a promoiety include, but are not limited to, amines (primary and secondary), hydroxyls, sulfanyls (thiols), carboxyls, carbonyls, phenols, catechols, diols, alkynes, phosphates, etc. Myriad progroups suitable for masking such functional groups to yield promoieties that are cleavable under the desired conditions of use are known in the art. All of these progroups, alone or in combinations, may be included in the prodrugs of the invention. Specific examples of promoieties that yield primary or secondary amine groups that can be included in the prodrugs of the invention include, but are not limited to, amides, ureas, imines, ureas, phosphenyls, phosphoryls and sulfenyls. Specific examples of promoieties that yield sulfanyl groups that can be included in the prodrugs of the invention include, but are not limited to, thioethers, for example S-methyl derivatives (monothio, dithio, oxythio, aminothio acetals), silyl thioethers, thioesters, thiocarbonates, thioureas, asymmetrical disulfides, etc. Specific examples of promoieties that cleave to yield hydroxyl groups that can be included in the prodrugs of the invention include, but are not limited to, sulfonates, esters and carbonates. Specific examples of promoieties that yield carboxyl groups that can be included in the prodrugs of the invention included, but are not limited to, esters (including silyl esters, oxamic acid esters and thioesters), amides and hydrazides.

In another aspect, the present invention provides compositions comprising one or more compounds and/or prodrugs of the invention and an appropriate carrier, excipient or diluent. The exact nature of the carrier, excipient or diluent will depend upon the desired use for the composition, and may range from being suitable or acceptable for veterinary uses to being suitable or acceptable for human use.

In still another aspect, the present invention provides intermediates useful for synthesizing the pyridine compounds and prodrugs of the invention as described herein, including salts, hydrates, solvates and N-oxides thereof, wherein Y, p, q, X and A are as previously defined for structural formula (I).

In yet another aspect, the present invention provides methods of synthesizing the pyridine compounds and prodrugs of the invention as described herein, including salts, hydrates, solvates and N-oxides thereof, wherein Y, p, q, X and A are as previously defined for structural formula (I).

The pyridine compounds of the invention are potent inhibitors of degranulation of immune cells, such as mast, basophil, neutrophil and/or eosinophil cells. Thus, in still another aspect, the present invention provides methods of regulating, and in particular inhibiting, degranulation of such cells. The method generally involves contacting a cell that degranulates with an amount of a pyridine compound or prodrug of the invention, or an acceptable salt, hydrate, solvate, N-oxide and/or composition thereof, effective to regulate or inhibit degranulation of the cell. The method may be practiced in in vitro contexts or in in vivo contexts as a therapeutic approach towards the treatment or prevention of diseases characterized by, caused by or associated with cellular degranulation.

While not intending to be bound by any theory of operation, biochemical data confirm that the pyridine compounds exert their degranulation inhibitory effect, at least in part, by blocking or inhibiting the signal transduction cascade(s) initiated by crosslinking of the high affinity Fc receptors for IgE ("FcεRI") and/or IgG ("FcγRI"). Indeed, the pyridine compounds are potent inhibitors of both FcεRI-mediated and FcγRI-mediated degranulation. As a consequence, the pyridine compounds may be used to inhibit these Fc receptor signalling cascades in any cell type expressing such FcεRI and/or FcγRI receptors including but not limited to macrophages, mast, basophil, neutrophil and/or eosinophil cells.

The methods also permit the regulation of, and in particular the inhibition of, downstream processes that result as a consequence of activating such Fc receptor signaling cascade(s). Such downstream processes include, but are not limited to, FcεRI-mediated and/or FcγRI-mediated degranulation, cytokine production and/or the production and/or release of lipid mediators such as leukotrienes and prostaglandins. The method generally involves contacting a cell expressing an Fc receptor, such as one of the cell types discussed above, with an amount of a pyridine compound or prodrug of the invention, or an acceptable salt, hydrate, solvent, N-oxide and/or composition thereof, effective to regulate or inhibit the Fc receptor signaling cascade and/or a downstream process effected by the activation of this signaling cascade. The method may be practiced in in vitro contexts or in in vivo contexts as a therapeutic approach towards the treatment or prevention of diseases characterized by, caused by or associated with the Fc receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present invention provides methods of treating and/or preventing diseases characterized by, caused by or associated with the release of chemical mediators as a consequence of activating Fc receptor signaling cascades, such as FcεRI and/or FcγRI-signaling cascades. The methods may be practiced in animals in veterinary contexts or in humans. The methods generally involve administering to an animal subject or human an amount of a pyridine compound or prodrug of the invention, or an acceptable salt, hydrate, solvate, N-oxide and/or composition thereof, effective to treat or prevent the disease. As discussed previously, activation of the FcεRI or FcγRI receptor signaling cascade in certain immune cells leads to the release and/or synthesis of a variety of chemical substances that are pharmacological mediators of a wide variety of diseases. Any of these diseases may be treated or prevented according to the methods of the invention.

For example, in mast cells and basophil cells, activation of the FcεRI or FcγRI signaling cascade leads to the immediate (i.e., within 1-3 min. of receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders and certain gastrointestinal disorders.

The immediate release of the preformed mediators via degranulation is followed by the release and/or synthesis of a variety of other chemical mediators, including, among other things, platelet activating factor (PAF), prostaglandins and leukotrienes (e.g., LTC4) and the de novo synthesis and release of cytokines such as TNFα, IL-4, IL-5, IL-6, IL-13, etc. The first of these two processes occurs approximately 3-30 min. following receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of inflammation and inflammatory diseases (e.g., osteoarthritis, inflammatory bowel disease, ulcerative colitis, Crohn's disease, idiopathic inflammatory bowel disease, irritable bowel syndrome, spastic colon, etc.), low grade scarring (e.g., scleroderma, increased fibrosis, keloids, post-surgical scars, pulmonary fibrosis, vascular spasms, migraine, reperfusion injury and post myocardial infarction), and sicca complex or syndrome. All of these diseases may be treated or prevented according to the methods of the invention.

Additional diseases which can be treated or prevented according to the methods of the invention include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD) and diseases of the gut such as inflammatory bowel syndrome (spastic colon).

The pyridine compounds of the invention are also potent inhibitors of the tyrosine kinase Syk kinase. Thus, in still another aspect, the present invention provides methods of regulating, and in particular inhibiting, Syk kinase activity. The method generally involves contacting a Syk kinase or a cell comprising a Syk kinase with an amount of a pyridine compound or prodrug of the invention, or an acceptable salt, hydrate, solvate, N-oxide and/or composition thereof, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method may be practiced in in vitro contexts or in in vivo contexts as a therapeutic approach towards the treatment or prevention of diseases characterized by, caused by or associated with Syk kinase activity.

Figure 2:
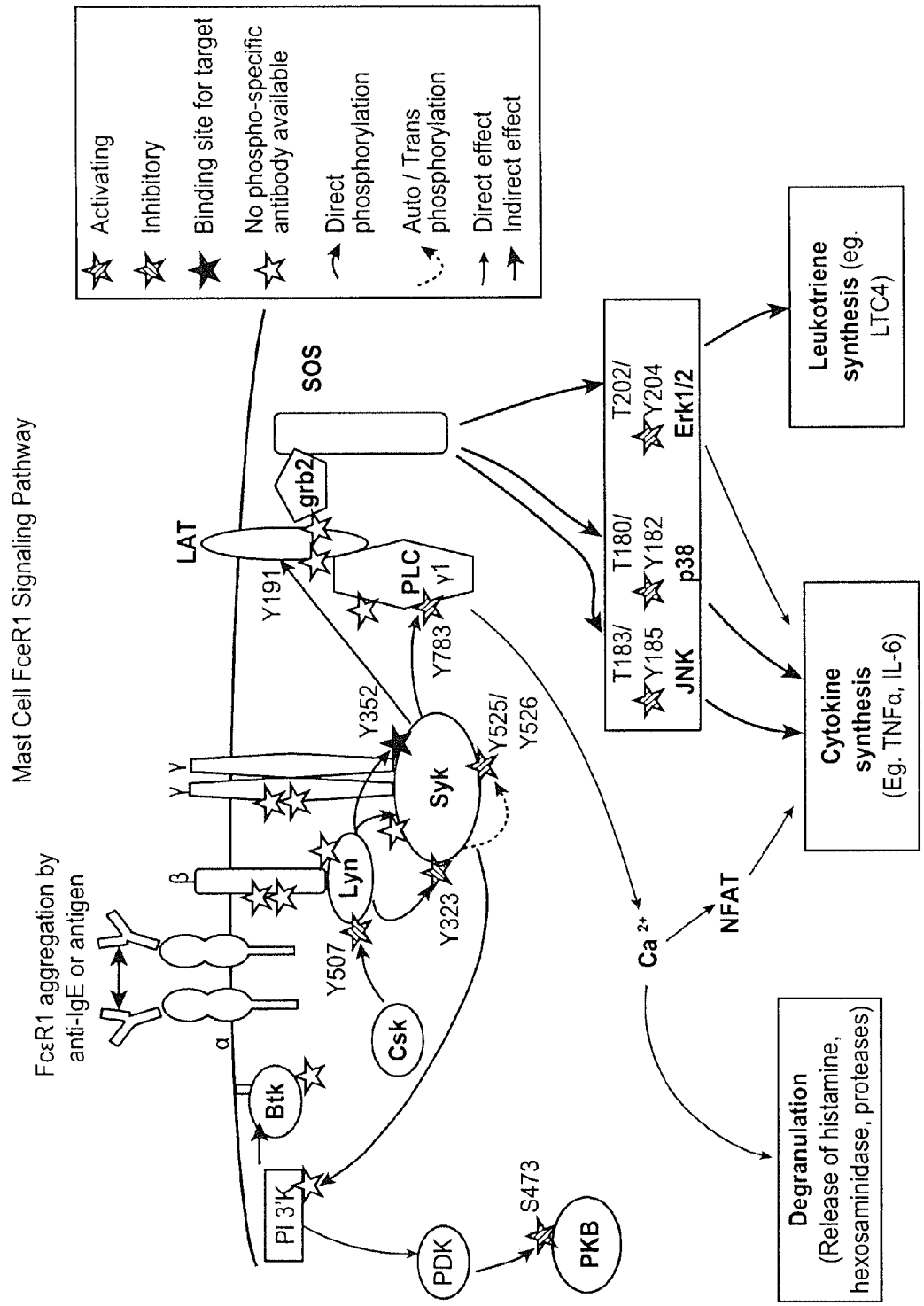

While not intending to be bound by any particular theory of operation, it is believed that the pyridine compounds of the invention inhibit cellular degranulation and/or the release of other chemical mediators primarily by inhibiting Syk kinase that gets activated through the gamma chain homodimer of FcεRI (see, e.g., FIG. 2). This gamma chain homodimer is shared by other Fc receptors, including FcγRI, FcγRIII and FcαRI. For all of these receptors, intracellular signal transduction is mediated by the common gamma chain homodimer. Binding and aggregation of those receptors results in the recruitment and activation of tyrosine kinases such as Syk kinase. As a consequence of these common signaling activities, the pyridine compounds described herein may be used to regulate, and in particular inhibit, the signaling cascades of Fc receptors having this gamma chain homodimer, such as FcεRI, FcγRI, FcγRIII and FcαRI, as well as the cellular responses elicited through these receptors.

Syk kinase is known to play a critical role in other signaling cascades. For example, Syk kinase is an effector of B-cell receptor (BCR) signaling (Turner et al., 2000, Immunology Today 21:148-154) and is an essential component of integrin beta(1), beta(2) and beta(3) signaling in neutrophils (Mocsai et al., 2002, Immunity 16:547-558). As the pyridine compounds described herein are potent inhibitors of Syk kinase, they can be used to regulate, and in particular inhibit, any signaling cascade where Syk plays a role, such as, fore example, the Fc receptor, BCR and integrin signaling cascades, as well as the cellular responses elicited through these signaling cascades. The particular cellular response regulated or inhibited will depend, in part, on the specific cell type and receptor signaling cascade, as is well known in the art. Non-limiting examples of cellular responses that may be regulated or inhibited with the pyridine compounds include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Thus, in another aspect, the present invention provides methods of regulating, and in particular inhibiting, signal transduction cascades in which Syk plays a role. The method generally involves contacting a Syk-dependent receptor or a cell expressing a Syk-dependent receptor with an amount of a pyridine compound or prodrug of the invention, or an acceptable salt, hydrate, solvate, N-oxide and/or composition thereof, effective to regulate or inhibit the signal transduction cascade. The methods may also be used to regulate, and in particular inhibit, downstream processes or cellular responses elicited by activation of the particular Syk-dependent signal transduction cascade. The methods may be practiced to regulate any signal transduction cascade where Syk is not known or later discovered to play a role. The methods may be practiced in in vitro contexts or in in vivo contexts as a therapeutic approach towards the treatment or prevention of diseases characterized by, caused by or associated with activation of the Syk-dependent signal transduction cascade. Non-limited examples of such diseases include those previously discussed.

Cellular and animal data also confirm that the pyridine compounds of the invention may also be used to treat or prevent autoimmune diseases and/or symptoms of such diseases. The methods generally involve administering to a subject suffering from an autoimmune disease or at risk of developing an autoimmune disease an amount of a pyridine method or prodrug of the invention, or an acceptable salt, N-oxide, hydrate, solvate or composition thereof, effective to treat or prevent the autoimmune disease and/or its associated symptoms. Autoimmune diseases that can be treated or prevented with the pyridine compounds include those diseases that are commonly associated with nonanaphylactic hypersensitivity reactions (Type II, Type III and/or Type IV hypersensitivity reactions) and/or those diseases that are mediated, at least in part, by activation of the FcγR signaling cascade in monocyte cells. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

5. BRIEF DESCRIPTION OF THE FIGURES

Figure 3:
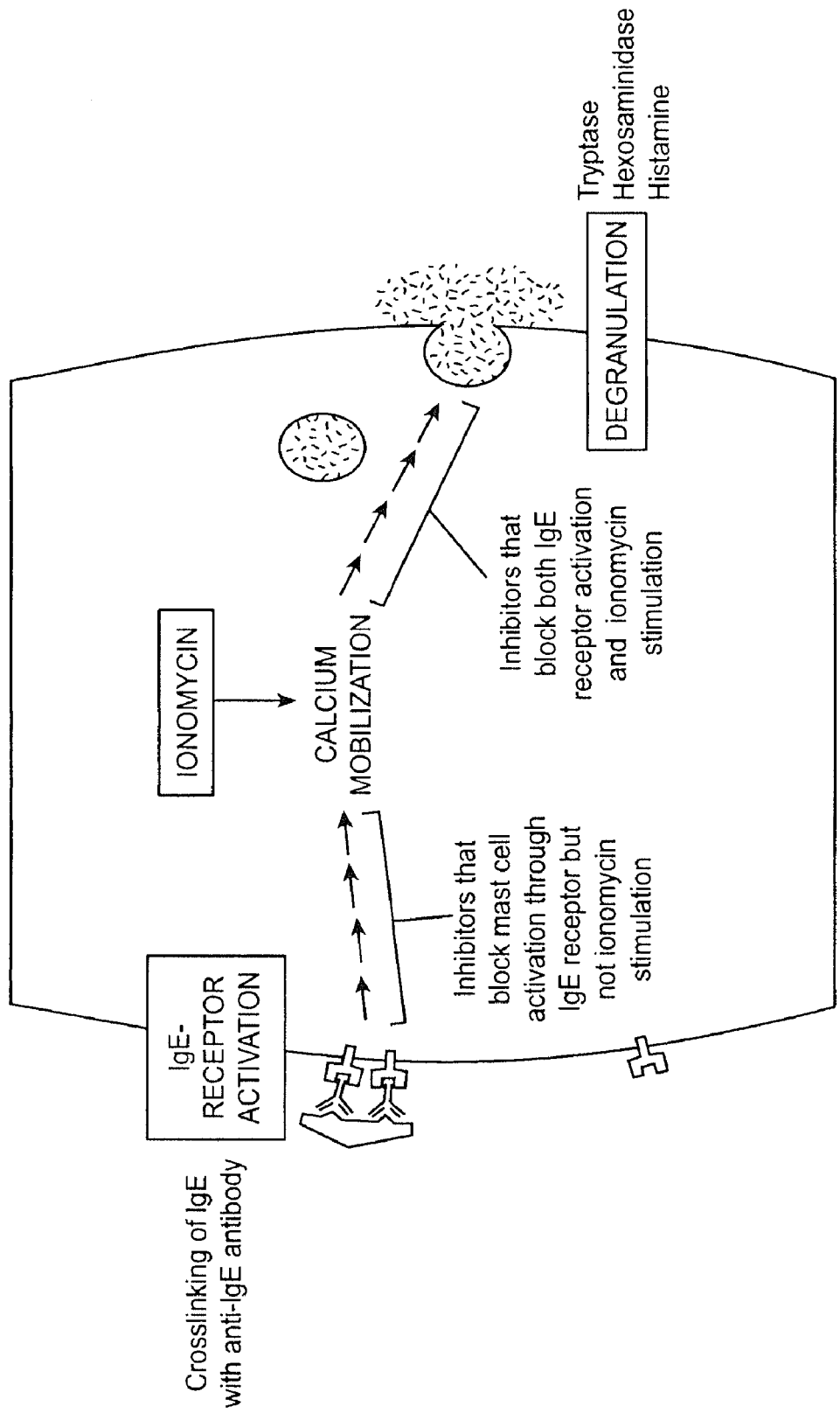

FIG. 1 provides a cartoon illustrating allergen-induced production of IgE and consequent release of preformed and other chemical mediators from mast cells;

FIG. 2 provides a cartoon illustrating the FcεR1 signal transduction cascade leading to degranulation of mast and/or basophil cells; and FIG. 3 provides a cartoon illustrating the putative points of action of compounds that selectively inhibit upstream FcεRI-mediated degranulation and compounds that inhibit both FcεRI-mediated and ionomycin-induced degranulation.

6. DETAILED DESCRIPTION

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Electron Withdrawing Group" refers to those substituents that have a —I relative to hydrogen. These substituents include, for example, $NR_3^+$, $SR_2^+$, $NH_3^+$, —$NO_2$, —$SO_2R$, —CN —$SO_2Ar$, —COOH, —F, —Cl, —Br, —I, —Oar, —COOR, —OR, —COR, —SH, —SR, —OH, —CCR, —Ar and —C=$CR_2$, wherein each R, individually, is a hydrogen, an alkyl or an aryl.

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Specifically excluded from the definition of "parent heteroaromatic ring system" are benzene rings fused to cyclic polyalkylene glycols such as cyclic polyethylene glycols. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active pyridine compound (drug) that requires a transformation under the conditions of use, such as within the body, to release the active pyridine drug. Prodrugs are frequently, but not necessarily, pharmacologically inactive until converted into the active drug. Prodrugs are typically obtained by masking a functional group in the pyridine drug believed to be in part required for activity with a progroup (defined below) to form a promoiety which undergoes a transformation, such as cleavage, under the specified conditions of use to release the functional group, and hence the active pyridine drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active pyridine compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, urea, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Nitrogen protecting groups and nitrogen pro-drugs of the invention may include lower alkyl groups as well as amides, ureas, etc. Other specific examples of suitable progroups and their respective promoieties will be apparent to those of skill in the art.

"Progroup" refers to a type of protecting group that, when used to mask a functional group within an active pyridine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Fc Receptor" refers to a member of the family of cell surface molecules that binds the Fc portion (containing the specific constant region) of an immunoglobulin. Each Fc receptor binds immunoglobulins of a specific type. For example the Fcα receptor ("FcαR") binds IgA, the FcεR binds IgE and the FcγR binds IgG.

The FcαR family includes the polymeric Ig receptor involved in epithelial transport of IgA/IgM, the mycloid specific receptor RcαRI (also called CD89), the Fcα/μR and at least two alternative IgA receptors (for a recent review see Monteiro & van de Winkel, 2003, Annu. Rev. Immunol, advanced e-publication. The FcαRI is expressed on neutrophils, eosinophils, moncytes/macrophages, dendritic cells and kupfer cells. The FcαRI includes one alpha chain and the FcR gamma homodimer that bears an activation motif (ITAM) in the cytoplasmic domain and phosphorylates Syk kinase.

The FcεR family includes two types, designated FcεRI and FcεRII (also known as CD23). FcεRI is a high affinity receptor (binds IgE with an affinity of about $10^{10}M^{-1}$) found on mast, basophil and eosinophil cells that anchors monomeric IgE to the cell surface. The FcεRI possesses one alpha chain, one beta chain and the gamma chain homodimer discussed above. The FcεRII is a low affinity receptor expressed on mononuclear phagocytes, B lymphocytes, eosinophils and platelets. The FcεRII comprises a single polypeptide chain and does not include the gamma chain homodimer.

The FcγR family includes three types, designated FcγRI (also known as CD64), FcγRII (also known as CD32) and FcγRIII (also known as CD16). FcγRI is a high affinity receptor (binds IgG1 with an affinity of $10^8M^{-1}$) found on mast, basophil, mononuclear, neutrophil, eosinophil, deudritic and phagocyte cells that anchors nomomeric IgG to the cell surface. The FcγRI includes one alpha chain and the gamma chain dimer shared by FcαRI and FcεRI.

The FcγRII is a low affinity receptor expressed on neutrophils, monocytes, eosinophils, platelets and B lymphocytes. The FcγRII includes one alpha chain, and does not include the gamma chain homodimer discussed above.

The FcγRIII is a low affinity (bindes IgG1 with an affinity of $5 \times 10^5M^{-1}$) expressed on NK, eosinophil, macrophage, neutrophil and mast cells. It comprises one alpha chain and the gamma homodimer shared by FcαRI, FcεRI and FcγRI.

Skilled artisans will recognize that the subunit structure and binding properties of these various Fc receptors, cell types expressing them, are not completely characterized. The above discussion merely reflects the current state-of-the-art regarding these receptors (see, e.g., Immunobiology: The Immune System in Health & Disease, 5$^{th}$ Edition, Janeway et al., Eds, 2001, ISBN 0-8153-3642-x, FIG. 9.30 at pp. 371), and is not intended to be limiting with respect to the myriad receptor signaling cascades that can be regulated with the compounds described herein.

"Fc Receptor-Mediated Degranulation" or "Fc Receptor-Induced Degranulation" refers to degranulation that proceeds via an Fc receptor signal transduction cascade initiated by crosslinking of an Fc receptor.

"IgE-Induced Degranulation" or "FcεRI-Mediated Degranulation" refers to degranulation that proceeds via the IgE receptor signal transduction cascade initiated by crosslinking of FcεR1-bound IgE. The crosslinking may be induced by an IgE-specific allergen or other multivalent binding agent, such as an anti-IgE antibody. Referring to FIG. 2, in mast and/or basophil cells, the FcεRI signaling cascade leading to degranulation may be broken into two stages: upstream and downstream. The upstream stage includes all of the processes that occur prior to calcium ion mobilization (illustrated as "Ca$^{2+}$" in FIG. 2; see also FIG. 3). The downstream stage includes calcium ion mobilization and all processes downstream thereof. Compounds that inhibit FcεRI-mediated degranulation may act at any point along the FcεRI-mediated signal transduction cascade. Compounds that selectively inhibit upstream FcεRI-mediated degranulation act to inhibit that portion of the FcεRI signaling cascade upstream of the point at which calcium ion mobilization is induced. In cell-based assays, compounds that selectively inhibit upstream FcεRI-mediated degranulation inhibit degranulation of cells such as mast or basophil cells that are activated or stimulated with an IgE-specific allergen or binding agent (such as an anti-IgE antibody) but do not appreciably inhibit degranulation of cells that are activated or stimulated with degranulating agents that bypass the FcεRI signaling pathway, such as, for example the calcium ionophores ionomycin and A23187.

"IgG-Induced Degranulation" or "FcγRI-Mediated Degranulation" refers to degranulation that proceeds via the FcγRI signal transduction cascade initiated by crosslinking of FcγRI-bound IgG. The crosslinking may be induced by an IgG-specific allergen or another multivalent binding agent, such as an anti-IgG or fragment antibody. Like the FcεRI signaling cascade, in mast and basophil cells the FcγRI signaling cascade also leads to degranulation which may be broken into the same two stages: upstream and downstream. Similar to FcεRI-mediated degranulation, compounds that selectively inhibit upstream FcγRI-mediated degranulation act upstream of the point at which calcium ion mobilization is induced. In cell-based assays, compounds that selectively inhibit upstream FcγRI-mediated degranulation inhibit degranulation of cells such as mast or basophil cells that are activated or stimulated with an IgG-specific allergen or binding agent (such as an anti-IgG antibody or fragment) but do not appreciably inhibit degranulation of cells that are activated or stimulated with degranulating agents that bypass the FcγRI signaling pathway, such as, for example the calcium ionophores ionomycin and A23187.

"Ionophore-Induced Degranulation" or "Ionophore-Mediated Degranulation" refers to degranulation of a cell, such as a mast or basophil cell, that occurs upon exposure to a calcium ionophore such as, for example, ionomycin or A23187.

"Syk Kinsase" refers to the well-known 72 kDa non-receptor (cytoplasmic) spleen protein tyrosine kinase expressed in B-cells and other hematopoetic cells. Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al., 2001, J. Biochem. (Tokyo) 130:177-

186); see also Turner et al., 2000, Immunology Today 21:148-154). Syk kinase has been extensively studied as an effector of B-cell receptor (BCR) signaling (Turner et al., 2000, supra). Syk kinase is also critical for tyrosine phosphorylation of multiple proteins which regulate important pathways leading from immunoreceptors, such as $Ca^{2+}$ mobilization and mitogen-activated protein kinase (MAPK) cascades (see, e.g., FIG. 2) and degranulation. Syk kinase also plays a critical role in integrin signaling in neutrophils (see, e.g., Mocsai et al. 2002, Immunity 16:547-558).

As used herein, Syk kinase includes kinases from any species of animal, including but not limited to, homosapiens, simian, bovine, porcine, rodent, etc., recognized as belonging to the Syk family. Specifically included are isoforms, splice variants, allelic variants, mutants, both naturally occuring and man-made. The amino acid sequences of such Syk kinases are well known and available from GENBANK. Specific examples of mRNAs encoding different isoforms of human Syk kinase can be found at GENBANK accession no. gi|21361552|ref|NM_003177.21, gi|496899|emb|Z29630.1|HSSYKPTK[496899] and gi|15030258|gb|BC01399.1|BC01399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Syk mimics," are expected to catalyze phosphorylation of substrates phosphorylated by Syk. Thus, it will be appreciated that such Syk mimics, signal transduction cascades in which such Syk mimics play a role and biological responses effected by such Syk mimics and Syk mimic-dependent signaling cascades may be regulated, and in particular inhibited, with the pyridine compounds described herein.

"Syk-Dependent Signaling Cascade" refers to a signal transduction cascade in which Syk kinase plays a role. Non-limiting examples of such Syk-dependent signaling cascades include the FcαRI, FcεRI, FcγRI, FcγRIII, BCR and integrin signaling cascades.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

6.1 The Substituted Pyridine Compounds

The compounds of the invention are generally pyridine compounds according to structural formula (I):

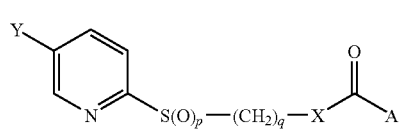
(I)

including pharmaceutically acceptable salts, hydrates, solvates and N-oxides thereof, wherein:

Y is selected from the group consisting of —OH, —SH, —Cn, —C(O)H, —$NO_2$, halo, fluoro, chloro, bromo, iodo, lower alkyl, substituted lower alkyl, lower heteroalkyl, substituted lower heteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, lower haloalkoxy, monohalomethoxy, dihalomethoxy, trihalomethoxy, trifluoromethoxy, amino, lower di- or monoalkylamino, substituted lower di- or monoalkylamino, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, thiocarbamoyl, substituted thiocarbamoyl, carbamates, substituted ureas, thioureas, substituted thioureas, sulfamoyl, substituted sulfamoyl, cycloalkylimides, substituted cycloalkylimides, isoindole-1,3-diones, substituted isoindole-1,3-diones, phthalimide and substituted phthalimides;

p is 0, 1 or 2;

q is an integer between and including 1 through 6;

X is O, NH or $NR^3$ $R^3$ is an alkyl, aryl, or a progroup; and

A is selected from the group consisting of alkyl, substituted alkyl, alkoxy, substituted alkoxy, aryl and substituted aryl.

In a first embodiment, Y is an electron withdrawing group, i.e., —$NO_2$, —$NH_2$, $NHR^1$, $NR^1R^2$, a carbamate, a substituted carbamate, a urea, a substituted urea, a cycloalkylimide, a phthalimide or a substituted phthalimide. Each $R^1$ and $R^2$ individually is an alkyl, aryl or a progroup and p, q, X, $R^3$ and A are as defined above.

In a second embodiment, Y is an electron withdrawing group, i.e., —$NO_2$, $NH_2$, $NHR^1$, $NR^1R^2$, a carbamate, a substituted carbamate, urea, a substituted urea, a cycloalkylimide, a phthalimide or a substituted phthalimide, $R^1$, $R^2$, $R^3$, p, q, X and A are as defined above, with the provisio that

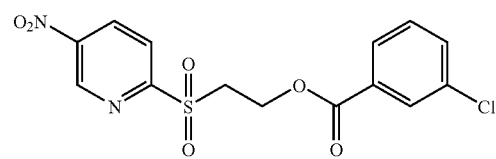

is not included.

In a third embodiment, Y is a urea according to the structural formula:

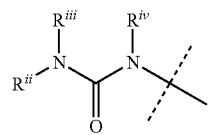

wherein $R^{ii}$, $R^{iii}$ and $R^{iv}$ are each, independently of one another, selected from hydrogen, an alkyl, a substituted alkyl, an aryl and a substituted aryl and $R^3$, p, q, X and A are as defined above. Suitable ureas include those where $R^{ii}$ and $R^{iii}$ are each hydrogen atoms and $R^{iv}$ is an aryl or substituted aryl or an alkyl, such as methyl, ethyl or propyl group.

In a fourth embodiment, Y is a cycloalkylimide according to the structural formula:

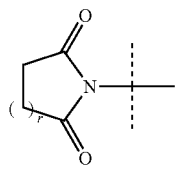

wherein r is 0 through 10 and R³, p, q, X and A are as defined above. In certain embodiments r is 2 or 3.

In a fifth embodiment, Y is an isoindole-1,3-dione-2-yl according to the structural formula:

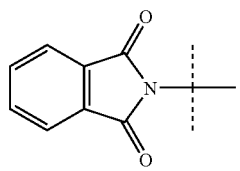

wherein the 4-, 5-, 6- or 7-position(s) can be further independently substituted and R³, p, q, X and A are as defined above.

In a sixth embodiment, Y is —NO₂ and R³, p, q, X and A are as defined above.

In a seventh embodiment, Y is an electron withdrawing group, i.e., —NO₂, NH₂, NHR¹, NR¹R², a carbamate, a substituted carbamate, a urea, a substituted urea, a cycloalkylimide, a phthalimide or a substituted phthalimide, R¹, R², R³, q, X and A are as defined above and p is 2.

In an eighth embodiment, Y is an electron withdrawing group, i.e., —NO₂, NH₂, NHR¹, NR¹R², a carbamate, a substituted carbamate, a urea, a substituted urea, a cycloalkylimide, a phthalimide or a substituted phthalimide, R¹, R², R³, p, X and A are as defined above and q is 2.

In a ninth embodiment, Y is an electron withdrawing group, i.e., —NO₂, NH₂, NHR¹, NR¹R², a carbamate, a substituted carbamate, a urea, a substituted urea, a cycloalkylimide, a phthalimide or a substituted phthalimide, R¹, R², R³, p, q and A are as defined above and X is an oxygen atom.

In a tenth embodiment, Y is an electron withdrawing group, i.e., —NO₂, NH₂, NHR¹, NR¹R², a carbamate, a substituted carbamate, a urea, a substituted urea, a cycloalkylimide, a phthalimide or a substituted phthalimide, R¹, R², R³, p, q, and X are as defined above and A is an alkyl group or an alkoxy group (thus forming a urea). Examples include methyl and ethyl groups as well as t-butoxy.

In an eleventh embodiment, Y is an electron withdrawing group, i.e., —NO₂, NH₂, NHR¹, NR¹R², a carbamate, a substituted carbamate, a urea, a substituted urea, a cycloalkylimide, a phthalimide or a substituted phthalimide, R¹, R², R³, p, q, and X are as defined above and A is an aryl group or a substituted aryl group. Suitable examples include a phenyl ring that can be substituted at one or more positions. Suitable substituents about the phenyl ring include —OH, —SH, —Cn, —C(O)H, —NO₂, azide, halo, fluoro, chloro, bromo, iodo, lower alkyl, substituted lower alkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, urea, substituted urea, carbamoyl, substituted carbamoyl, thiocarbamoyl, substituted thiocarbamoyl, ureas, substituted ureas, thioureas, substituted thioureas, sulfamoyl and substituted sulfamoyl.

In a twelfth embodiment, Y is —NO₂, p is 2, q is 2, X is O and A is a monosubstituted phenyl ring. In certain embodiments, the substituent on the phenyl ring is a halogen, trifluoromethyl or trifluoromethoxy.

Also specifically described are combinations of the above first through twelfth embodiments.

Exemplary pyridine compounds of the invention are noted in TABLES 1 and 2, infra.

Those of skill in the art will appreciate that the pyridine compounds described herein may include functional groups that can be masked with progroups to create prodrugs. Such prodrugs are usually, but need not be, pharmacologically inactive until converted into their active drug form. Indeed, some of the active pyridine compounds described in TABLES 1 and 2, include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, pyridine compounds that include ester moieties may be considered prodrugs of their corresponding carboxylic acid, regardless of whether the ester form is pharmacologically active. Referring to TABLES 1 and 2, hydrolysable moieties containing pyridine compounds of the invention can be active in their various "prodrug" forms.

In the prodrugs of the invention, any available functional moiety may be masked with a progroup to yield a prodrug. Functional groups within the pyridine compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs of the invention.

Those of skill in the art will appreciate that some of the compounds and prodrugs of the invention, as well as the various compound species specifically described and/or illustrated herein, may exhibit the phenomena of tautomerism, conformational isomerism, geometric isomerism and/or optical isomerism. For example, the compounds and prodrugs of the invention may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the compounds and prodrugs of the invention may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms.

Moreover, skilled artisans will appreciate that when lists of alternative substituents include members which, owing to valency requirements or other reasons, cannot be used to substitute a particular group, the list is intended to be read in context to include those members of the list that are suitable for substituting the particular group. For example, skilled artisans will appreciate that while all of the listed alternatives can be used to substitute an alkyl group, certain of the alternatives, such as =O, cannot be used to substitute a phenyl group. It is to be understood that only possible combinations of substituent-group pairs are intended.

Depending upon the nature of the various substituents, the pyridine compounds and prodrugs of the invention may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, cycloalkylsulfonic acids (e.g., camphorsulfonic acid), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion), an ammonium ion or coordinates with an organic base (e.g., ethanolamine, diethanolamine, triethanolamine, N-methylglucamine, morpholine, piperidine, dimethylamine, diethylamine, etc.).

The pyridine compounds and of the invention, as well as the salts thereof, may also be in the form of hydrates, solvates and N-oxides, as are well-known in the art.

6.2 Method of Synthesis

The compounds and prodrugs of the invention may be synthesized via a variety of synthetic routes using commercially available starting materials and/or starting materials prepared by synthetic methods as described herein.

Compounds prepared by the methods of the invention are included in TABLES 1 and 2, infra.

6.3 Inhibition of Fc Receptor Signal Cascades

Active pyridine compounds of the invention inhibit Fc receptor signalling cascades that lead to, among other things, degranulation of cells. As a specific example, the compounds inhibit the FcεRI and/or FcγRI signal cascades that lead to degranulation of immune cells such as neutrophil, eosinophil, mast and/or basophil cells. Both mast and basophil cells play a central role in allergen-induced disorders, including, for example, allergic rhinitis and asthma. Referring to FIG. 1, upon exposure allergens, which may be, among other things, pollen or parasites, allergen-specific IgE antibodies are synthesized by B-cells activated by IL-4 (or IL-13) and other messengers to switch to IgE class specific antibody synthesis. These allergen-specific IgEs bind to the high affinity FcεRI. Upon binding of antigen, the FcεRI-bound IgEs are cross-linked and the IgE receptor signal transduction pathway is activated, which leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAF) and prostaglandins (e.g., PGD2) and a series of cytokines, including TNF-α, IL-4, IL-13, IL-5, IL-6, IL-8, GMCSF, VEGF and TGF-β. The release and/or synthesis of these mediators from mast and/or basophil cells accounts for the early and late stage responses induced by allergens, and is directly linked to downstream events that lead to a sustained inflammatory state. Although the present invention has been described with reference to preferred embodiments, persons skilled in the art will recognize that changes may be made in form and detail without departing from the spirit and scope of the invention.

The molecular events in the FcεRI signal transduction pathway that lead to release of preformed mediators via degranulation and release and/or synthesis of other chemical mediators are well-known and are illustrated in FIG. 2. Referring to FIG. 2, the FcεRI is a heterotetrameric receptor composed of an IgE-binding alpha-subunit, a beta subunit, and two gamma subunits (gamma homodimer). Cross-linking of FcεRI-bound IgE by multivalent binding agents (including, for example IgE-specific allergens or anti-IgE antibodies or fragments) induces the rapid association and activation of the Src-related kinase Lyn. Lyn phosphorylates immunoreceptor tyrosine-based activation motifs (ITAMS) on the intracellular beta and gamma subunits, which leads to the recruitment of additional Lyn to the beta subunit and Syk kinase to the gamma homodimer. These receptor-associated kinases, which are activated by intra- and intermolecular phosphorylation, phosphorylate other components of the pathway, such as the Btk kinase, LAT, and phospholipase C-gamma (PLC-gamma). Activated PLC-gamma initiates pathways that lead to protein kinase C activation and $Ca^{2+}$ mobilization, both of which are required for degranulation. FcεR1 cross-linking also activates the three major classes of mitogen activated protein (MAP) kinases, i.e. ERK1/2, JNK1/2, and p38. Activation of these pathways is important in the transcriptional regulation of proinflammatory mediators, such as TNF-α and IL-6, as well as the lipid mediator leukotriene CA (LTC4).

Although not illustrated, the FcγRI signaling cascade is believed to share some common elements with the FcεRI signaling cascade. Importantly, like FcεRI, the FcγRI includes a gamma homodimer that is phosphorylated and recruits Syk, and like FcεRI, activation of the FcγRI signaling cascade leads to, among other things, degranulation. Other Fc receptors that share the gamma homodimer, and which can be regulated by the active pyridine compounds include, but are not limited to, FcαRI and FcγRIII.

The ability of the pyridine compounds of the invention to inhibit Fc receptor signaling cascades may be simply determined or confirmed in in vitro assays. Suitable assays for confirming inhibition of FcεRI-mediated degranulation are provided in the Examples section. In one typical assay, cells capable of undergoing FcεRI-mediated degranulation, such as mast or basophil cells, are first grown in the presence of IL-4, Stem Cell Factor (SCF), IL-6 and IgE to increase expression of the FcεRI, exposed to a pyridine test compound of the invention and stimulated with anti-IgE antibodies (or, alternatively, an IgE-specific allergen). Following incubation, the amount of a chemical mediator or other chemical agent released and/or synthesized as a consequence of activating the FcεRI signaling cascade may be quantified using standard techniques and compared to the amount of the mediator or agent released from control cells (i.e., cells that are stimulated but that are not exposed to test compound). The concentration of test compound that yields a 50% reduction in the quantity of the mediator or agent measured as compared to control cells is the $IC_{50}$ of the test compound. The origin of the mast or basophil cells used in the assay will depend, in part, on the desired use for the compounds and will be apparent to those of skill in the art. For example, if the compounds will be used to treat or prevent a particular disease in humans, a convenient source of mast or basophil cells is a human or other animal which constitutes an accepted or known clinical model for the particular disease. Thus, depending upon the particular application, the mast or basophil cells may be derived from a wide variety of animal sources, ranging from, for example, lower mammals such as mice and rats, to dogs, sheep and other mammals commonly employed in clinical testing, to higher mammals such as monkeys, chimpanzees and apes, to humans. Specific examples of cells suitable for carrying out the in vitro assays include, but are not limited to, rodent or human basophil cells, rat basophil leukemia cell lines, primary mouse mast cells (such as bone marrow-derived mouse mast cells "BMMC") and primary human mast cells isolated from cord blood ("CHMC") or other tissues such as lung. Methods for isolating and culturing these cell types are well-known or are provided in the Examples section (see, e.g., Demo et al., 1999, Cytometry 36(4):340-348 and copending application Ser. No. 10/053,355, filed Nov. 8, 2001, the disclosures of which are incorporated herein by reference). Of course, other types of immune cells that degranulate upon activation of the FcεRI signaling cascade may also be used, including, for example, eosinophils.

As will be recognized by skilled artisans, the mediator or agent quantified is not critical. The only requirement is that it be a mediator or agent released and/or synthesized as a consequence of initiating or activating the Fc receptor signaling cascade. For example, referring to FIG. 1, activation of the FcεRI signaling cascade in mast and/or basophil cells leads to numerous downstream events. For example, activation of the FcεRI signal cascade leads to the immediate release (i.e., within 1-3 min. following receptor activation) of a variety of preformed chemical mediators and agents via degranulation. Thus, in one embodiment, the mediator or agent quantified may be specific to granules (i.e., present in granules but not in the cell cytoplasm generally). Examples of granule-specific mediators or agents that can be quantified to determine and/or confirm the activity of a pyridine compound of the invention include, but are not limited to, granule-specific enzymes such as hexosaminidase and tryptase and granule-specific components such as histamine and serotonin. Assays for quantifying such factors are well-known, and in many instances are commercially available. For example, tryptase and/or hexosaminidase release may be quantified by incubating the cells with cleavable substrates that fluoresce upon cleavage and quantifying the amount of fluorescence produced using conventional techniques. Such cleavable fluorogenic substrates are commercially available. For example, the fluorogenic substrates Z-Gly-Pro-Arg-AMC (Z=benzyloxycarbonyl; AMC=7-amino-4-methylcoumarin; BIOMOL Research Laboratories, Inc., Plymouth Meeting, Pa. 19462, Catalog No. P-142) and Z-Ala-Lys-Arg-AMC (Enzyme Systems Products, a division of ICN Biomedicals, Inc., Livermore, Calif. 94550, Catalog No. AMC-246) can be used to quantify the amount of tryptase released. The fluorogenic substrate 4-methylumbelliferyl-N-acetyl-β-D-glucosaminide (Sigma, St. Louis, Mo., Catalog #69585) can be used to quantify the amount of hexosaminidase released. Histamine release may be quantified using a commercially available enzyme-linked immunosorbent assay (ELISA) such as Immunotech histamine ELISA assay #IM2015 (Beckman-Coulter, Inc.). Specific methods of quantifying the release of tryptase, hexosaminidase and histamine are provided in the Examples section. Any of these assays may be used to determine or confirm the activity of the pyridine compounds of the invention.

Referring again to FIG. 1, degranulation is only one of several responses initiated by the FcεRI signaling cascade. In addition, activation of this signaling pathway leads to the de novo synthesis and release of cytokines and chemokines such as IL-4, IL-5, IL-6, TNF-α, IL-13 and MIP1-α), and release of lipid mediators such as leukotrienes (e.g., LTC4), platelet activating factor (PAF) and prostaglandins. Accordingly, the pyridine compounds of the invention may also be assessed for activity by quantifying the amount of one or more of these mediators released and/or synthesized by activated cells.

Unlike the granule-specific components discussed above, these "late stage" mediators are not released immediately following activation of the FcεRI signaling cascade. Accordingly, when quantifying these late stage mediators, care should be taken to insure that the activated cell culture is incubated for a time sufficient to result in the synthesis (if necessary) and release of the mediator being quantified. Generally, PAF and lipid mediators such as leukotriene C4 are released 3-30 min. following FcεRI activation. The cytokines and other late stage mediators are released approx. 4-8 hrs. following FcεRI activation. Incubation times suitable for a specific mediator will be apparent to those of skill in the art. Specific guidance and assays are provided in the Examples section.

The amount of a particular late stage mediator released may be quantified using any standard technique. In one embodiment, the amount(s) may be quantified using ELISA assays. ELISA assay kits suitable for quantifying the amount of TNFα, IL-4, IL-5, IL-6 and/or IL-13 released are available from, for example, Biosource International, Inc., Camarillo, Calif. 93012 (see, e.g., Catalog Nos. KHC3011, KHC0042, KHC0052, KHC0061 and KHC0132). ELISA assay kits suitable for quantifying the amount of leukotriene C4 (LTC4) released from cells are available from Cayman Chemical Co., Ann Arbor, Mich. 48108 (see, e.g., Catalog No. 520211).

Typically, active pyridine compounds of the invention will exhibit $IC_{50}$'s with respect to FcεRI-mediated degranulation and/or mediator release or synthesis of about 20 μM or lower, as measured in an in vitro assay, such as one of the in vitro assays described above or in the Examples section. Of course, skilled artisans will appreciate that compounds which exhibit lower $IC_{50}$'s, for example on the order of 10 μM, 1 μM, 100 nM, 10 nM, 1 nM, or even lower, are particularly useful.

Skilled artisans will also appreciate that the various mediators discussed above may induce different adverse effects or exhibit different potencies with respect to the same adverse effect. For example, the lipid mediator LTC4 is a potent vasoconstrictor—it is approximately 1000-fold more potent at inducing vasoconstriction than histamine. As another example, in addition to mediating atopic or Type I hypersensitivity reactions, cytokines can also cause tissue remodeling and cell proliferation. Thus, although compounds that inhibit release and/or synthesis of any one of the previously discussed chemical mediators are useful, skilled artisans will appreciate that compounds which inhibit the release and/or synthesis of a plurality, or even all, of the previously described mediators find particular use, as such compounds are useful for ameliorating or avoiding altogether a plurality, or even all, of the adverse effects induced by the particular mediators. For example, compounds which inhibit the release of all three types of mediators—granule-specific, lipid and cytokine—are useful for treating or preventing immediate Type I hypersensitivity reactions as well as the chronic symptoms associated therewith.

Compounds of the invention capable of inhibiting the release of more than one type of mediator (e.g., granule-specific or late stage) may be identified by determining the $IC_{50}$ with respect to a mediator representative of each class using the various in vitro assays described above (or other equivalent in vitro assays). Compounds of the invention which are capable of inhibiting the release of more than one mediator type will typically exhibit an $IC_{50}$ for each mediator type tested of less than about 20 μM. For example, a compound which exhibits an $IC_{50}$ of 1 μM with respect to histamine release ($IC_{50}^{histamine}$) and an $IC_{50}$ of 1 nM with respect to leukotriene LTC4 synthesis and/or release ($IC_{50}^{LTC4}$) inhibits both immediate (granule-specific) and late stage mediator release. As another specific example, a compound that exhibits an $IC_{50}^{tryptase}$ of 10 μM, an $IC_{50}^{LTC4}$ of 1 μM and an $IC_{50}^{IL-4}$ of 1 μM inhibits immediate (granule-specific), lipid and cytokine mediator release. Although the above specific examples utilize the $IC_{50}$'s of one representative mediator of each class, skilled artisans will appreciate that the $IC_{50}$'s of a plurality, or even all, mediators comprising one or more of the classes may be obtained. The quantity(ies) and identity(ies) of mediators for which $IC_{50}$ data should be ascertained for a particular compound and application will be apparent to those of skill in the art.

Similar assays may be utilized to confirm inhibition of signal transduction cascades initiated by other Fc receptors, such as FcαRI, FcγRI and/or FcγRIII signaling, with routine modification. For example, the ability of the compounds to inhibit FcγRI signal transduction may be confirmed in assays similar to those described above, with the exception that the FcγRI signaling cascade is activated, for example by incubating the cells with IgG and an IgG-specific allergen or antibody, instead of IgE and an IgE-specific allergen or antibody. Suitable cell types, activating agents and agents to quantify to confirm inhibition of other Fc receptors, such as Fc receptors that comprise a gamma homodimer, will be apparent to those of skill in the art.

One particularly useful class of compounds includes those pyridine compounds that inhibit the release of immediate granule-specific mediators and late stage mediators with approximately equivalent $IC_{50}$s. By approximately equivalent is meant that the $IC_{50}$s for each mediator type are within about a 10-fold range of one another. Another particularly useful class of compounds includes those pyridine compounds that inhibit the release of immediate granule-specific mediators, lipid mediators and cytokine mediators with approximately equivalent $IC_{50}$s. In a specific embodiment, such compounds inhibit the release of the following mediators with approximately equivalent $IC_{50}$s: histamine, tryptase, hexosaminidase, IL-4, IL-5, IL-6, IL-13, TNFα and LTC4. Such compounds are particularly useful for, among other things, ameliorating or avoiding altogether both the early and late stage responses associated with atopic or immediate Type I hypersensitivity reactions.

Ideally, the ability to inhibit the release of all desired types of mediators will reside in a single compound. However, mixtures of compounds can also be identified that achieve the same result. For example, a first compound which inhibits the release of granule specific mediators may be used in combination with a second compound which inhibits the release and/or synthesis of cytokine mediators.

In addition to the FcεRI or FcγRI degranulation pathways discussed above, degranulation of mast and/or basophil cells can be induced by other agents. For example, ionomycin, a calcium ionophore that bypasses the early FcεRI or FcγRI signal transduction machinery of the cell, directly induces a calcium flux that triggers degranulation. Referring again to FIG. 2, activated PLCγ initiates pathways that lead to, among other things, calcium ion mobilization and subsequent degranulation. As illustrated, this $Ca^{2+}$ mobilization is triggered late in the FcεRI signal transduction pathway. As mentioned above, and as illustrated in FIG. 3, ionomycin directly induces $Ca^{2+}$ mobilization and a $Ca^{2+}$ flux that leads to degranulation. Other ionophores that induce degranulation in this manner include A23187. The ability of granulation-inducing ionophores such as ionomycin to bypass the early stages of the FcεRI and/or FcγRI signaling cascades may be used as a counter screen to identify active compounds of the invention that specifically exert their degranulation-inhibitory activity by blocking or inhibiting the early FcεRI or FcγRI signaling cascades, as discussed above. Compounds which specifically inhibit such early FcεRI or FcγRI-mediated degranulation inhibit not only degranulation and subsequent rapid release of histamine, tryptase and other granule contents, but also inhibit the pro-inflammatory activation pathways causing the release of TNFα, IL-4, IL-13 and the lipid mediators such as LTC4. Thus, compounds which specifically inhibit such early FcεRI and/or FcγRI-mediated degranulation block or inhibit not only acute atopic or Type I hypersensitivity reactions, but also late responses involving multiple inflammatory mediators.

Compounds of the invention that specifically inhibit early FcεRI and/or FcγRI-mediated degranulation are those compounds that inhibit FcεRI and/or FcγRI-mediated degranulation (for example, have an $IC_{50}$ of less than about 20 μM with respect to the release of a granule-specific mediator or component as measured in an in vitro assay with cells stimulated with an IgE or IgG binding agent) but that do not appreciably inhibit ionophore-induced degranulation. In one embodiment, compounds are considered to not appreciably inhibit ionophore-induced degranulation if they exhibit an $IC_{50}$ of ionophore-induced degranulation of greater than about 20 μM, as measured in an in vitro assay. Of course, active compounds that exhibit even higher $IC_{50}$s of ionophore-induced degranulation, or that do not inhibit ionophore-induced degranulation at all, are particularly useful. In another embodiment, compounds are considered to not appreciably inhibit ionophore-induced degranulation if they exhibit a greater than 10-fold difference in their $IC_{50}$s of FcεRI and/or FcγRI-mediated degranulation and ionophore-induced degranulation, as measured in an in vitro assay. Assays suitable for determining the $IC_{50}$ of ionophore-induced degranulation include any of the previously-described degranulation assays, with the modification that the cells are stimulated or activated with a degranulation-inducing calcium ionophore such as ionomycin or A23187 (A.G. Scientific, San Diego, Calif.) instead of anti-IgE antibodies or an IgE-specific allergen. Specific assays for assessing the ability of a particular pyridine compound of the invention to inhibit ionophore-induced degranulation are provided in the Examples section.

As will be recognized by skilled artisans, compounds which exhibit a high degree of selectivity of FcεRI-mediated degranulation find particular use, as such compounds selectively target the FcεRI cascade and do not interfere with other degranulation mechanisms. Similarly, compounds which exhibit a high degree of selectivity of FcγRI-mediated degranulation find particular use, as such compounds selectively target the FcγRI cascade and do not interfere with other degranulation mechanisms. Compounds which exhibit a high degree of selectivity are generally 10-fold or more selective for FcεRI- or FcγRI-mediated degranulation over ionophore-induced degranulation, such as ionomycin-induced degranulation.

Accordingly, the activity of the pyridine compounds of the invention may also be confirmed in biochemical or cellular assays of Syk kinase activity. Referring again to FIG. 2, in the FcεRI signaling cascade in mast and/or basophil cells, Syk kinase phosphorylates LAT and PLC-gammal, which leads to, among other things, degranulation. Any of these activities may be used to confirm the activity of the pyridine compounds of the invention. In one embodiment, the activity is confirmed by contacting an isolated Syk kinase, or an active fragment thereof with a pyridine compound in the presence of a Syk kinase substrate (e.g., a synthetic peptide or a protein that is known to be phophorylated by Syk in a signaling cascade) and assessing whether the Syk kinase phosphorylated the substrate. Alternatively, the assay may be carried out with cells that express a Syk kinase. The cells may express the Syk kinase endogenously or they may be engineered to express a recombinant Syk kinase. The cells may optionally also express the Syk kinase substrate. Cells suitable for performing such confirmation assays, as well as methods of engineering suitable cells will be apparent to those of skill in the art. Specific examples of biochemical and cellular assays suitable for confirming the activity of the pyridine compounds are provided in the Examples section.

Generally, compounds that are Syk kinase inhibitors will exhibit an $IC_{50}$ with respect to a Syk kinase activity, such as the ability of Syk kinase to phosphorylate a synthetic or endogenous substrate, in an in vitro or cellular assay in the range of about 20 μM or less. Skilled artisans will appreciate that compounds that exhibit lower IC50s, such as in the range of 10 μM, 1 μM, 100 nM, 10 nM, 1 nM, or even lower, are particularly useful.

6.4 Uses and Compositions

As previously discussed, the active compounds of the invention inhibit Fc receptor signaling cascades, especially those Fc receptors including a gamma homodimer, such as the FcεRI and/or FcγRI signaling cascades, that lead to, among other things, the release and/or synthesis of chemical mediators from cells, either via degranulation or other processes. As also discussed, the active compounds are also potent inhibitors of Syk kinase. As a consequence of these activities, the active compounds of the invention may be used in a variety of in vitro, in vivo and ex vivo contexts to regulate or inhibit Syk kinase, signaling cascades in which Syk kinase plays a role, Fc receptor signaling cascades, and the biological responses effected by such signaling cascades. For example, in one embodiment, the compounds may be used to inhibit Syk kinase, either in vitro or in vivo, in virtually any cell type expressing Syk kinase. They may also be used to regulate signal transduction cascades in which Syk kinase plays a role. Such Syk-dependent signal transduction cascades include, but are not limited to, the FcεRI, FcγRI, FcγRIII, BCR and integrin signal transduction cascades. The compounds may also be used in vitro or in vivo to regulate, and in particular inhibit, cellular or biological responses effected by such Syk-dependent signal transduction cascades. Such cellular or biological responses include, but are not limited to, respiratory burst, cellular adhesion, cellular degranulation, cell spreading, cell migration, cell aggregation, phagcytosis, cytokine synthesis and release, cell maturation and $Ca^{2+}$ flux. Importantly, the compounds may be used to inhibit Syk kinase in vivo as a therapeutic approach towards the treatment or prevention of diseases mediated, either wholly or in part, by a Syk kinase activity. Non-limiting examples of Syk kinase mediated diseases that may be treated or prevented with the compounds are those discussed in more detail, below.

In another embodiment, the active compounds may be used to regulate or inhibit the Fc receptor signaling cascades and/or FcεRI- and/or FcγRI-mediated degranulation as a therapeutic approach towards the treatment or prevention of diseases characterized by, caused by and/or associated with the release or synthesis of chemical mediators of such Fc receptor signaling cascades or degranulation. Such treatments may be administered to animals in veterinary contexts or to humans. Diseases that are characterized by, caused by or associated with such mediator release, synthesis or degranulation, and that can therefore be treated or prevented with the active compounds include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel syndrome, spastic colon and inflammatory bowel disease), inflammation and scarring.

In addition to the myriad diseases discussed above, cellular and animal empirical data confirm that the pyridine compounds described herein are also useful for the treatment or prevention of autoimmune diseases, as well as the various symptoms associated with such diseases. The types of autoimmune diseases that may be treated or prevented with the pyridine compounds generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

As discussed previously, Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the pyridine compounds of the invention. In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated. Many of these symptoms, as well as their underlying disease states, result as a consequence of activating the FcγR signaling cascade in monocyte cells. As the pyridine compounds described herein are potent inhibitors of such FcγR signaling in monocytes and other cells, the methods find use in the treatment and/or prevention of myriad adverse symptoms associated with the above-listed autoimmune diseases.

As a specific example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dentritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The methods may be used to treat or ameliorate any one, several or all of these symptoms of RA. Thus, in the context of RA, the methods are considered to provide therapeutic benefit (discussed more generally, infra) when a reduction or amelioration of any of the symptoms commonly associated with RA is achieved, regardless of whether the treatment results in a concomitant treatment of the underlying RA and/or a reduction in the amount of circulating rheumatoid factor ("RF").

As another specific example, systemic lupus erythematosis ("SLE") is typically associated with symptoms such as fever, joint pain (arthralgias), arthritis, and serositis (pleurisy or pericarditis). In the context of SLE, the methods are considered to provide therapeutic benefit when a reduction or amelioration of any of the symptoms commonly associated with SLE are achieved, regardless of whether the treatment results in a concomitant treatment of the underlying SLE.

As another specific example, multiple sclerosis ("MS") cripples the patient by disturbing visual acuity; stimulating double vision; disturbing motor functions affecting walking and use of the hands; producing bowel and bladder incontinence; spasticity; and sensory deficits (touch, pain and temperature sensitivity). In the context of MS, the methods are considered to provide therapeutic benefit when an improvement or a reduction in the progression of any one or more of the crippling effects commonly associated with MS is achieved, regardless of whether the treatment results in a concomitant treatment of the underlying MS.

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The active compounds may be administered per se in the form of prodrugs or as pharmaceutical compositions, comprising an active compound or prodrug.

Pharmaceutical compositions comprising the active compounds of the invention (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

Another specific example of an aqueous suspension suitable for administration of the compounds via inhalation, and in particular for such administration of a compound of the invention, contains 1-20 mg/mL of the compound or prodrug, 0.1-1% (v/v) Polysorbate 80 (TWEEN®80), 50 mM citrate and/or 0.9% sodium chloride.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. No. 5,407,713.; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

6.5 Effective Dosages

The active compound(s) or prodrug(s) of the invention, or compositions thereof, will generally be used in an amount effective to achieve the intended result, for example in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound may be administered to a patient at risk of developing one of the previously described diseases. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities which trigger asthma attacks to lessen the severity of, or avoid altogether, an asthmatic episode.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," *In: Goodman and Gilman's The Pharmaceutical Basis of Therapeutics*, Chapter 1, pp. 1-46, latest edition, Pagamonon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6): 1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001, Invest. Ophthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-5511. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Ordinarily skilled artisans can routinely adapt such information to determine dosages suitable for human administration. Additional suitable animal models are described in the Examples section.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compounds(s) that exhibit high therapeutic indices are preferred.

The invention having been described, the following examples are offered by way of illustration and not limitation.

7. EXAMPLES

7.1 Substituted Pyridine Compounds

A variety of substituted pyridine compounds were prepared based on procedures described herein. Such compounds are depicted in TABLES 1 and 2. The following synthetic methods are representative for the synthesis of pyridine compounds described throughout the application.

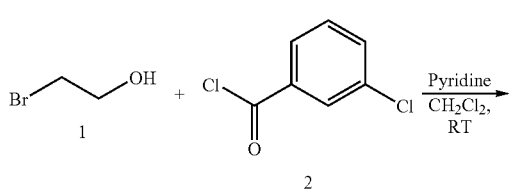

Scheme 1

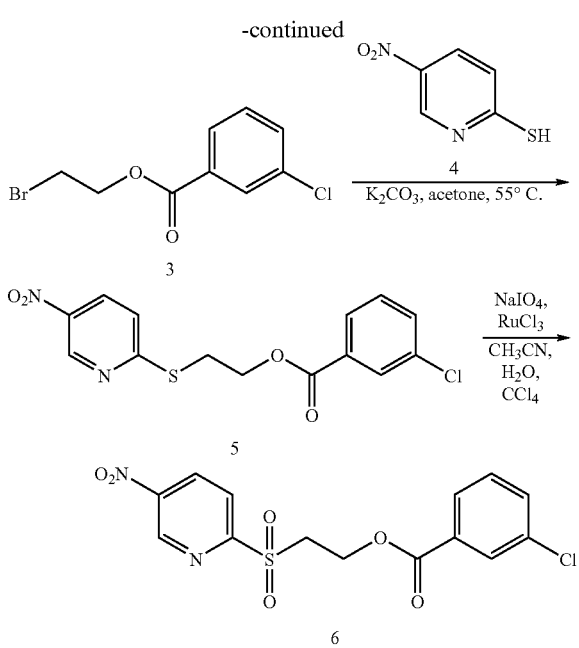

2-Bromoethyl-3-chlorobenzoate (3): To a solution of 3-chlorobenzoyl chloride (2) (0.21 g, 2.8 mmol) and pyridine (0.46 mL, 5.7 mmol) in anhydrous dichloromethane (10 mL) at room temperature was (dropwise) added 2-bromoethanol (1) (0.23 mL, 3.1 mmol). The reaction mixture was stirred for 2 h at room temperature and quenched with 1N HCl. The organic phase was washed with saturated aqueous solution of NaHCO$_3$, brine and then dried over anhydrous MgSO$_4$. The crude product was purified by silica gel chromatography to give 2-bromoethyl 3-chlorobenzoate (3) as colorless oil (0.64 g). $^1$H NMR (CDCl$_3$): δ 8.04 (t, J=1.8 Hz, 1H), 7.98-7.93 (m, 1H), 7.58-7.52 (m, 1H), 7.40 (t, J=8.4 Hz, 1H), 4.63 (t, J=6.0 Hz, 2H), 3.64 (t, J=6.0 Hz, 2H)

2-[(5-Nitro-2-pyridinyl)thio]ethyl-3-chlorobenzoate (5): A heterogeneous mixture of 2-mercapto-5-nitropyridine (4) (46 mg, 0.29 mmol), 2-bromoethyl-3-chlorobenzoate (3) (77 mg, 0.29 mmol), and K$_2$CO$_3$ (0.160 g, 1.1 mmol) in acetone (1 mL) was stirred at 55° C. for 5 h. The cooled reaction mixture was filtered through Celite®, concentrated, and then purified by silica gel chromatography to give 2-[(5-nitro-2-pyridinyl)thio]ethyl-3-chlorobenzoate (5) as a white solid. 1H NMR (CDCl3): δ 9.22 (d, J=1.8 Hz, 1H), 8.24 (dd, J=2.4 and 9.0 Hz, 1H), 7.95-7.91 (m, 1H), 7.90 (t, J=0.9 Hz, 1H), 7.56-7.51 (m, 1H), 7.39 (d, J=8.1 Hz, 1H), 7.34 (d, J=8.1 Hz, 1H), 4.61 (t, J=6.6 Hz, 2H), 3.68 (t, J=6.6 Hz, 2H)

2-[(5-Nitro-2-pyridinyl)sulfonyl]ethyl 3-chlorobenzoate (6): To a solution of 2-[(5-nitro-2-pyridinyl)thio]ethyl 3-chlorobenzoate (5) (30 mg, 0.089 mmol) in CCl$_4$, acetonitrile, and water (1:1:2, v/v; total volume: 0.8 mL)) were added NaIO$_4$ (59 mg, 0.27 mmol) and RuCl$_3$:H$_2$O (1.8 mg, 0.0089 mmol). After 3 h, the reaction mixture was diluted with equal amounts of water and ethyl acetate. The organic phase was washed with saturated aqueous solution of NaHCO$_3$ and brine. The crude product was purified by silica gel chromatography to provide 2-[(5-nitro-2-pyridinyl)sulfonyl]ethyl 3-chlorobenzoate (6) as a white solid. $^1$H NMR (DMSO-d$_6$): δ 9.37 (d, J=2.4 Hz, 1H), 8.66 (dd, J=2.4 and 9.0 Hz, 1H), 8.24 (d, J=8.1 Hz, 1H), 7.52-7.37 (m, 2H), 7.29 (ddd, J=1.5, 6.3, and 8.1 Hz, 1H), 4.60 (t, J=5.4 Hz, 2H), 4.11 (t, J=5.4 Hz, 2H); LCMS: purity: 97%; MS (m/e): 372(MH$^+$).

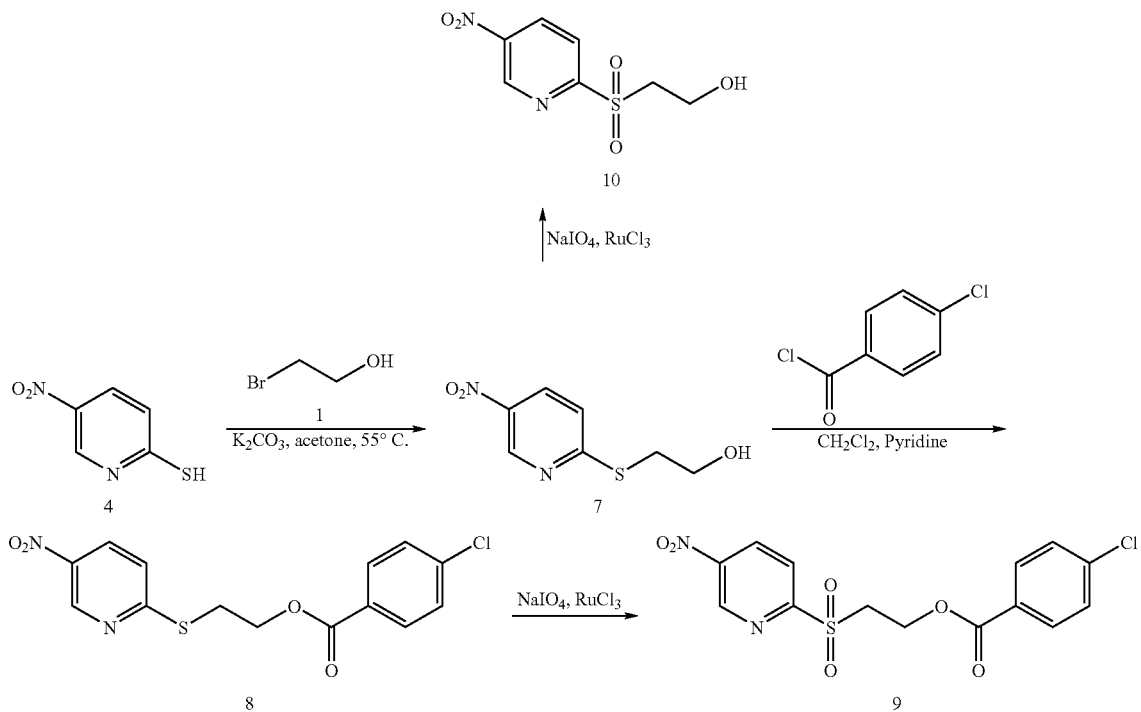

2-[(5-Nitro-2-pyridinyl)thio]ethanol (7): A heterogeneous mixture of 2-mercapto-5-nitropyridine (4) (0.50 g, 3.2 mmol), 2-bromoethanol (1) (0.238 mL, 3.3 mmol), and $K_2CO_3$ (2.0 g, 14 mmol) in acetone (11 mL) was stirred at 55° C. for 1 h. The cooled reaction mixture was filtered through Celite®, concentrated, and then purified by silica gel chromatography to give 2-[(5-nitro-2-pyridinyl)thio]ethanol (7) as an orange solid (0.545 g, 2.72 mmol). $^1H$ NMR (CDCl$_3$): δ 9.20 (d, J=3.0 Hz, 1H), 8.23 (dd, J=3.0 and 8.7 Hz, 1H), 7.36 (d, J=8.7 Hz, 1H), 3.94 (t, J=6.0 Hz, 2H), 3.46 (d, J=6.0 Hz, 2H); LCMS: purity: 96%; MS (m/e): 201(MH$^+$).

2-[(5-Nitro-2-pyridinyl)thio]ethyl 4-chlorobenzoate (8): A homogeneous mixture of 2-[(5-nitro-2-pyridinyl)thio]ethanol (7) (45 mg, 0.22 mmol), 4-chlorobenzoyl chloride (33 μL, 0.26 mmol) and pyridine (45 μL, 0.56 mmol) in anhydrous dichloromethane (1.5 mL) was stirred at room temperature for 48 h. The reaction mixture was quenched with 1N HCl and the organic phase was washed with saturated aqueous solution of NaHCO$_3$, brine and then dried over anhydrous MgSO$_4$. The crude product was purified by silica gel chromatography to give 2-[(5-nitro-2-pyridinyl)thio]ethyl 4-chlorobenzoate (8). LCMS: purity: 90%; MS (m/e): 340 (M$^+$)

2-[(5-Nitro-2-pyridinyl)sulfonyl]ethyl 4-chlorobenzoate (9): In like manner to the oxidation of 2-[(5-nitro-2-pyridinyl)thio]ethyl 2-chlorobenzoate (5) to give 2-[(5-nitro-2-pyridinyl)sulfonyl]ethyl 2-chlorobenzoate (6), the oxidation of 2-[(5-nitro-2-pyridinyl)thio]ethyl 4-chlorobenzoate (8) was accomplished to give 2-[(5-nitro-2-pyridinyl)sulfonyl]ethyl 4-chlorobenzoate (9). $^1H$ NMR (DMSO-d$_6$): δ 9.32 (d, J=2.4 Hz, 1H), 8.71 (dd, J=2.1 and 8.7 Hz, 1H), 8.26 (d, J=8.7 Hz, 1H), 7.51 (d, J=8.7 Hz, 2H), 7.43 (d, J=8.7 Hz, 2H), 4.63 (t, J=5.7 Hz, 2H), 4.14 (t, J=5.7 Hz, 2H); LCMS: purity: 93%; MS (m/e): 371(MH$^+$).

2-[(5-Nitropyridiny)sulfonyl]ethanol (10): In like manner to the oxidation of 2-[(5-nitro-2-pyridinyl)thio]ethyl 4-chlorobenzoate (8) to give 2-[(5-nitro-2-pyridinyl)sulfonyl]ethyl 4-chlorobenzoate (9), the oxidation of 2-[(5-nitro-2-pyridinyl)thio]ethanol (7) afforded 2-[(5-nitropyridiny)sulfonyl]ethanol (10). LCMS: purity: 95%; MS (m/e): 233 (MH$^+$).

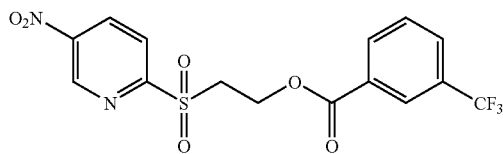

11

2-[(5-Nitro-2-pyridinyl)sulfonyl]ethyl 3-trifluoromethylbenzoate (11): In like manner to the synthesis of 2-[(5-nitro-2-pyridinyl)sulfonyl]ethyl 4-chlorobenzoate (9), the 2-[(5-nitro-2-pyridinyl)sulfonyl]ethyl 3-trifluoromethylbenzoate (11) was synthesized by O-acylation of 2-[(5-nitro-2-pyridinyl)thio]ethanol (7) with 3-trifluoromethylbenzoyl chloride followed by oxidation of the sulfur as described above. $^1H$ NMR (DMSO-d$_6$): δ 9.33 (d, J=3.6 Hz, 1H), 8.71 (dd, J=2.1 and 8.1 Hz, 1H), 8.30 (d, J=9.6 Hz, 1H), 7.99-7.94 (m, 1H), 7.88 (d, J=8.4 Hz, 1H), 7.47 (bs, 1H), 7.66 (t, J=7.8 Hz, 1H), 4.68 (t, J=5.4 Hz, 2H), 4.19 (t, J=5.4 Hz, 2H); LCMS: purity: 94%; MS (m/e): 404(M$^+$).

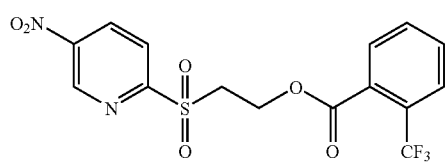

12

2-[(5-Nitro-2-pyridinyl)sulfonyl]ethyl-2-trifluoromethylbenzoate (12): In like manner to the synthesis of 2-[(5-nitro-2-pyridinyl)sulfonyl]ethyl 4-chlorobenzoate (9), the 2-[(5-nitro-2-pyridinyl)sulfonyl]ethyl 2-trifluoromethylbenzoate (12) was synthesized by O-acylation of 2-[(5-nitro-2-pyridinyl)thio]ethanol (7) with 2-trifluoromethylbenzoyl chloride followed by oxidation of the sulfur as described above. $^1H$ NMR (DMSO-d$_6$): δ 9.35 (d, J=2.4 Hz, 1H), 8.63 (dd, J=2.1 and 9.0 Hz, 1H), 8.21 (d, J=9.0 Hz, 1H), 7.80-7.65 (m, 3H), 7.56-7.51 (m, 1H), 4.60 (t, J=5.4 Hz, 2H), 4.09 (t, J=5.4 Hz, 2H); LCMS: purity: 94%; MS (m/e): 404(M$^+$).

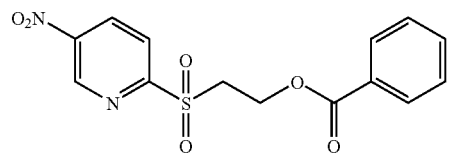

13

2[(5-Nitro-2-pyridinyl)sulfonyl]ethyl benzoate (13): In like manner to the synthesis of 2-[(5-nitro-2-pyridinyl)sulfonyl]ethyl 4-chlorobenzoate (9), 2-[(5-nitro-2-pyridinyl)sulfonyl]ethylbenzoate (13) was synthesized by O-acylation of 2-[(5-nitro-2-pyridinyl)thio]ethanol (7) with benzoyl chloride followed by oxidation of the sulfur as described above. $^1H$ NMR (CDCl$_3$): δ 9.21 (d, J=1.8 Hz, 1H), 8.52 (dd, J=2.4 and 8.7 Hz, 1H), 8.24 (d, J=8.7 Hz, 1H), 7.58 (d, J=8.1 Hz, 2H), 7.49 (t, J=7.5 Hz, 1H), 7.31 (d, J=8.1 Hz, 2H), 4.78 (t, J=5.4 Hz, 2H), 4.02 (t, J=5.4 Hz, 2H).

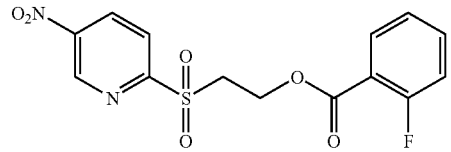

14

2-[(5-Nitro-2-pyridinyl)sulfonyl]ethyl 2-fluorobenzoate (14): In like manner to the synthesis of 2-[(5-nitro-2-pyridinyl)sulfonyl]ethyl 4-chlorobenzoate (9), 2-[(5-nitro-2-pyridinyl)sulfonyl]ethyl 2-fluorobenzoate (14) was synthesized by O-acylation of 2-[(5-nitro-2-pyridinyl)thio]ethanol (7) with 2-fluorobenzoyl chloride followed by oxidation of the sulfur as described above. $^1H$ NMR (CDCl$_3$): δ 9.29 (d, J=2.4 Hz, 1H), 8.55 (dd, J=2.7 and 8.7 Hz, 1H), 8.25 (d, J=8.4 Hz, 1H), 7.62 (dt, J=1.8 and 7.5 Hz, 1H), 7.52-7.43 (m, 1H), 7.11 (t, J=7.5 Hz, 1H), 7.01 (t, J=9.3 Hz, 1H), 4.78 (t, J=5.4 Hz, 2H), 3.99 (t, J=5.4 Hz, 2H).

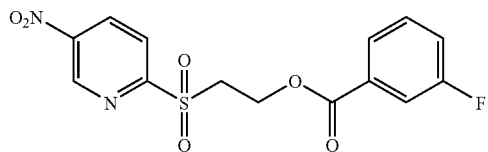

15

2-[(5-Nitro-2-pyridinyl)sulfonyl]ethyl 3-fluorobenzoate (15): In like manner to the synthesis of 2-[(5-nitro-2-pyridinyl)sulfonyl]ethyl 4-chlorobenzoate (9), 2-[(5-nitro-2-pyridinyl)sulfonyl]ethyl 3-fluorobenzoate (15) was synthesized by O-acylation of 2-[(5-nitro-2-pyridinyl)thio]ethanol (7) with 3-fluorobenzoyl chloride followed by oxidation of the sulfur as described above. $^1H$ NMR (CDCl$_3$): δ 9.31 (d, J=2.4 Hz, 1H), 8.63 (dd, J=2.1 and 8.7 Hz, 1H), 8.29 (d, J=8.1 Hz, 1H), 7.49 (td, J=1.2 and 7.8 Hz, 1H), 7.36–7.14 (m, 2H), 4.79 (t, J=5.4 Hz, 2H), 4.01 (t, J=5.4 Hz, 2H).

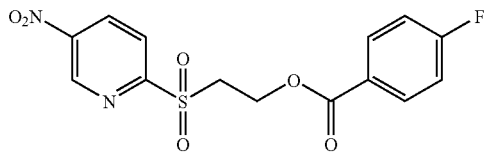

16

2-[(5-Nitro-2-pyridinyl)sulfonyl]ethyl 4-fluorobenzoate (16): In like manner to the synthesis of 2-[(5-nitro-2-pyridinyl)sulfonyl]ethyl 4-chlorobenzoate (9), 2-[(5-nitro-2-pyridinyl)sulfonyl]ethyl 4-fluorobenzoate (16) was synthesized by O-acylation of 2-[(5-nitro-2-pyridinyl)thio]ethanol (7) with 4-fluorobenzoyl chloride followed by oxidation of the sulfur as described above. $^1$H NMR (CDCl$_3$): δ 9.31 (d, J=2.4 Hz, 1H), 8.62 (dd, J=2.4 and 8.4 Hz, 1H), 8.29 (d, J=9.3 Hz, 1H), 7.76–7.70 (m, 2H), 7.05–6.98 (m 2H), 4.77 (t, J=5.4 Hz, 2H), 4.00 (d, J=5.4 Hz, 2H); LCMS: purity: 99%; MS (m/e): 355 (MH$^+$).

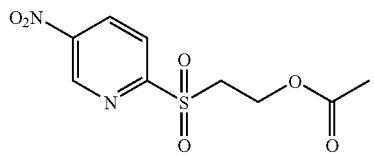

17

2-[(5-Nitro-2-pyridinyl)sulfonyl]ethyl acetate (17): In like manner to the synthesis of 2-[(5-nitro-2-pyridinyl)sulfonyl]ethyl 4-chlorobenzoate (9), 2-[(5-nitro-2-pyridinyl)sulfonyl]ethylacetate (17) was synthesized by O-acylation of 2-[(5-nitro-2-pyridinyl)thio]ethanol (7) with acetyl chloride followed by oxidation of the sulfur as described above. $^1$H NMR (CDCl$_3$): δ 9.52 (d, J=2.4 Hz, 1H), 8.76 (dd, J=2.4 and 8.7 Hz, 1H), 8.32 (d, J=7.5 Hz, 1H), 4.50 (t, J=6.0 Hz, 2H), 3.85 (t, J=6.0 Hz, 2H), 1.87 (s, 3H); LCMS: purity: 99%; MS (m/e): 275 (MH$^+$).

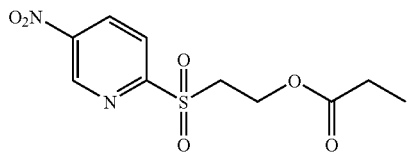

18

2-[(5-Nitro-2-pyridinyl)sulfonyl]ethyl propionate (18): In like manner to the synthesis of 2-[(5-nitro-2-pyridinyl)sulfonyl]ethyl 4-chlorobenzoate (9), 2-[(5-nitro-2-pyridinyl)sulfonyl]ethylpropionate (18) was synthesized by O-acylation of 2-[(5-nitro-2-pyridinyl)thio]ethanol (7) with propyl chloride followed by oxidation of the sulfur as described above. $^1$H NMR (CDCl$_3$): δ 9.52 (d, J=2.4 Hz, 1H), 8.76 (dd, J=2.4 and 8.7 Hz, 1H), 8.31 (d, J=8.7 Hz, 1H), 4.51 (t, J=6.0 Hz, 2H), 3.85 (t, J=6.0 Hz, 2H), 2.10 (q, J=7.5 Hz, 2H), 1.03 (t, J=7.5 Hz, 3H).

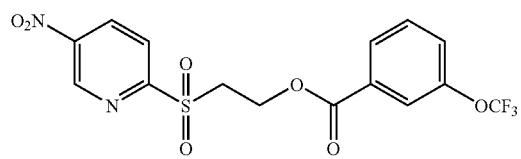

19

2-[(5-Nitro-2-pyridinyl)sulfonyl]ethyl 3-trifluoromethoxybenzoate (19): In like manner to the synthesis of 2-[(5-nitro-2-pyridinyl)sulfonyl]ethyl 4-chlorobenzoate (9), 2-[(5-nitro-2-pyridinyl)sulfonyl]ethyl-3-trifluoromethoxybenzoate (19) was synthesized by O-acylation of 2-[(5-nitro-2-pyridinyl)thio]ethanol (7) with 3-trifluorobenzoylchloride followed by oxidation of the sulfur as described above. $^1$H NMR (CDCl$_3$): δ 9.30 (d, J=1.8 Hz, 1H), 8.62 (dd, J=2.4 and 8.4 Hz, 1H), 8.29 (d, J=9.0 Hz, 1H), 7.69–7.64 (m, 1H), 7.51–7.38 (m, 3H), 4.81 (t, J=5.1 Hz, 2H), 4.02 (t, J=5.1 Hz, 2H); LCMS: purity: 99%; MS (m/e): 421 (MH$^+$).

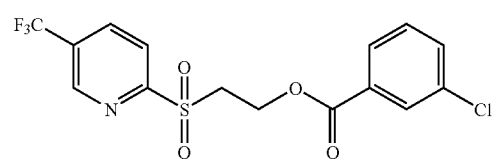

21

2-[(5-Trifluoromethyl-2-pyridinyl)-2-sulfonyl]ethyl 3-chlorobenzoate (21): In like manner to the synthesis of 2-[(5-nitro-2-pyridinyl)sulfonyl]ethyl 4-chlorobenzoate (9), 2-[(5-trifluoromethylpyridinyl)sulfonyl]ethyl-3-chlorobenzoate (21) was synthesized by O-acylation of 2-[(5-trifluoromethylpyridinyl)thio]ethanol with 3-chlorobenzoylchloride followed by oxidation of the sulfur as described above. $^1$H NMR (CDCl$_3$): δ 8.81 (d, J=2.1 Hz, 1H), 8.23 (d, J=8.1 Hz, 1H), 8.14 (dd, J=1.8 and 8.1 Hz, 1H), 7.64–7.48 (m, 3H), 7.29 (d, J=8.4 Hz, 1H), 4.78 (t, J=5.4 Hz, 2H), 3.99 (t, J=5.4 Hz, 2H). LCMS: purity: 96%; MS (m/e): 394 (M$^+$).

Scheme 3

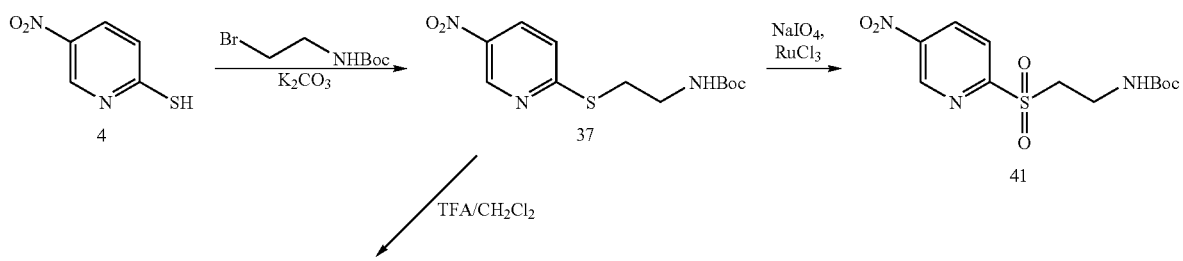

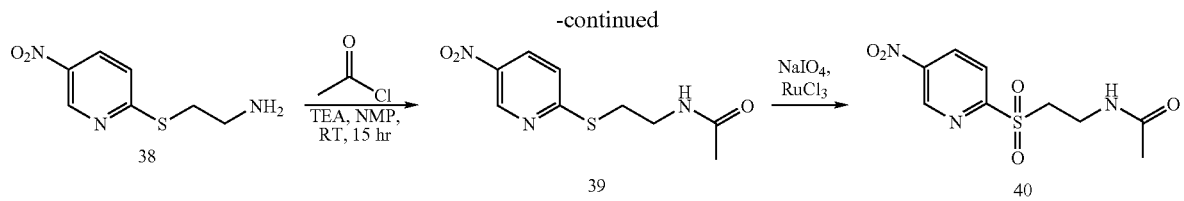

1-Amino-2-[(5-nitro-2-pyridinyl)thio]ethane (38): A heterogeneous solution of 2-mercapto-5-nitropyridine (96 mg, 0.62 mmol), N-tert-butoxycarbonyl-amino-2-bromoethane (0.14 g, 0.63 mmol), and $K_2CO_3$ (0.42 g, 3.0 mmol) in acetone (10 mL) was heated at 60° C. for 15 h. The cooled reaction mixture was filtered through Celite®, concentrated, and then purified by silica gel chromatography to give N-tert-butoxycarbonyl-amino-2-(5-nitro-2-pyridinylthio)ethane (37), which was treated with trifluoroacetic acid (5 mL) in dichloromethane (5 mL) at room temperature for 30 min. The reaction mixture was concentrated and then residue was suspended in dichloromethane, washed with saturated $NaHCO_3$ followed by brine, dried over anhydrous $MgSO_4$ and concentrated to give 1-amino-2-[(5-nitro-2-pyridinyl)thio]ethane (38) as a tan solid which was used without further purification. $^1$H NMR (DMSO-$d_6$): δ 9.21 (d, J=3.0 Hz, 1H), 8.41 (dd, J=2.4 and 8.7 Hz, 1H), 7.81 (bs, 2H), 7.65 (d, J=8.7 Hz, 1H), 3.44 (t, J=6.6 Hz, 2H), 3.12 (t, J=6.6 Hz, 2H).

N-[(2-{5-Nitro-2-pyridinyl}thio)ethylacetamide (39): To a solution of 1-amino-2-[(5-nitro-2-pyridinyl)thio]ethane (38) (24 mg, 0.12 mmol) and triethylamine (42 μL, 0.30 mmol) in N-methylpyrrolidine (1.0 mL) was added acetyl chloride (10 μL, 0.14 mmol) at room temperature, stirred for 15 h and then diluted with dichloromethane, the dichloromethane extract was washed with saturated aqueous solution of $NaHCO_3$ and brine and then dried over anhydrous $MgSO_4$. The crude product was purified by silica gel chromatography to give N-[(2-{5-nitro-2-pyridinyl}thio)ethyl]acetamide (39). $^1$H NMR (CDCl$_3$): δ 9.23 (d, J=1.8 Hz, 1H), 8.24 (dd, J=3.0 and 9.0 Hz, 1H), 7.35 (d, J=9.0 Hz, 1H), 3.58 (t, J=6.0 Hz, 2H), 3.41 (t, J=6.0 Hz, 2H), 1.97 (s, 3H)

N-[(2-{5-Nitro-2-pyridinylsulfonyl)ethyl]acetamide (40): The oxidation of N-[2-(5-nitro-2-pyridinyl}thio)ethyl]acetamide (39) to give N-[(2-{5-nitro-2-pyridinyl}sulfonyl)ethyl]acetamide (40) was accomplished in a manner analogous to the procedure used to synthesize 2-[(5-nitro-2-pyridinyl)sulfonyl]ethyl 3-chlorobenzoate (6), as per Scheme 1. LCMS: purity: 90%; MS (m/e): 273 (M$^+$)

2-[(2-{N-tert-Butoxycarbonylamino}ethyl)sulfonyl]-5-nitropyridine (41): The oxidation of N-tert-butoxycarbonylamino-2-(5-nitro-2-pyridinylthio)ethane (37) to give 2-[(2-{N-butoxycarbonylaminoethyl)sulfonyl]-5-nitropyridine (41) was accomplished in a manner analogous to the procedure used to synthesize 2-[(5-nitro-2-pyridinyl)sulfonyl] ethyl 3-chlorobenzoate (6), as per Scheme 1. $^1$H NMR (CDCl$_3$): δ 9.51 (d, J=2.4 Hz, 1H), 8.76 (dd, J=2.4 and 8.7 Hz, 1H), 8.32 (d, J=8.7 Hz, 1H), 5.01 (bs, 1H), 3.75-3.60 (m, 4H), 1.39 (s, 9H).

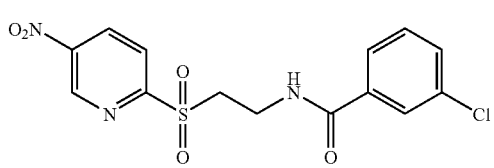

3-Chloro-N-[2-({5-nitro-2-pyridinyl}sulfonyl)ethyl]benzamide (42): In like manner to the preparation of N-[2-(5-nitro-2-pyridinylsulfonyl)ethyl]acetamide (40), the reaction of 1-amino-2-(5-nitro-2-pyridinylthio)ethane (38) with 3-chlorobenzoylchloride followed by oxidation gave 3-chloro-N-[2-({5-nitro-2-pyridinyl}sulfonyl)ethyl]benzamide (42). LCMS: purity: 94%; MS (m/e): 371 (MH$^+$).

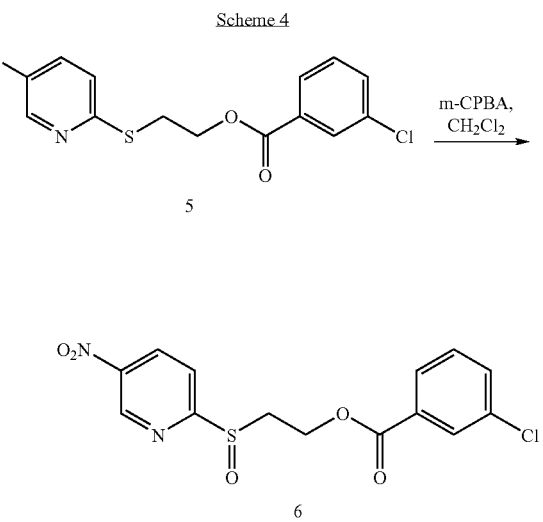

2-[(5-nitro-2-pyridinyl)sulfinyl]ethyl-3-chlorobenzoate (6): A solution of 2-(5-nitro-2-pyridinylthio)ethyl-3-chlorobenzoate, (5) [20 mg, 0.059 mmol; prepared according to the method outlined in Scheme 2; $^1$H NMR (CDCl$_3$): δ 9.22 (d, J=1.8 Hz, 1H), 8.24 (dd, J=2.4 and 9.0 Hz, 1H), 7.95-7.91 (m, 1H), 7.90 (t, J=0.9 Hz, 1H), 7.56-7.51 (m, 1H), 7.39 (d, J=8.1 Hz, 1H), 7.34 (d, J=8.1 Hz, 1H), 4.61 (t, J=6.6 Hz, 2H), 3.68 (t, J=6.6 Hz, 2H)] and m-chloroperbenzoate (m-CPBA) 50%, 21 mg, 0.060 mmol) was stirred at room temperature for 1.25 h. The reaction mixture was then diluted with dichloromethane and washed with saturated aqueous solution of $NaHCO_3$ and then dried over anhydrous $MgSO_4$. The crude product was purified by silica gel chromatography to give 2-[(5-nitro-2-pyridinyl)sulfinyl]ethyl-3-chlorobenzoate (6). LCMS: purity: 99%; MS (m/e): 355 (MH$^+$).

Similarly, compounds 100 through 103 can be prepared by the same methods as used for compound 5, with an appropriate change in starting material (compound 2).

Scheme 5

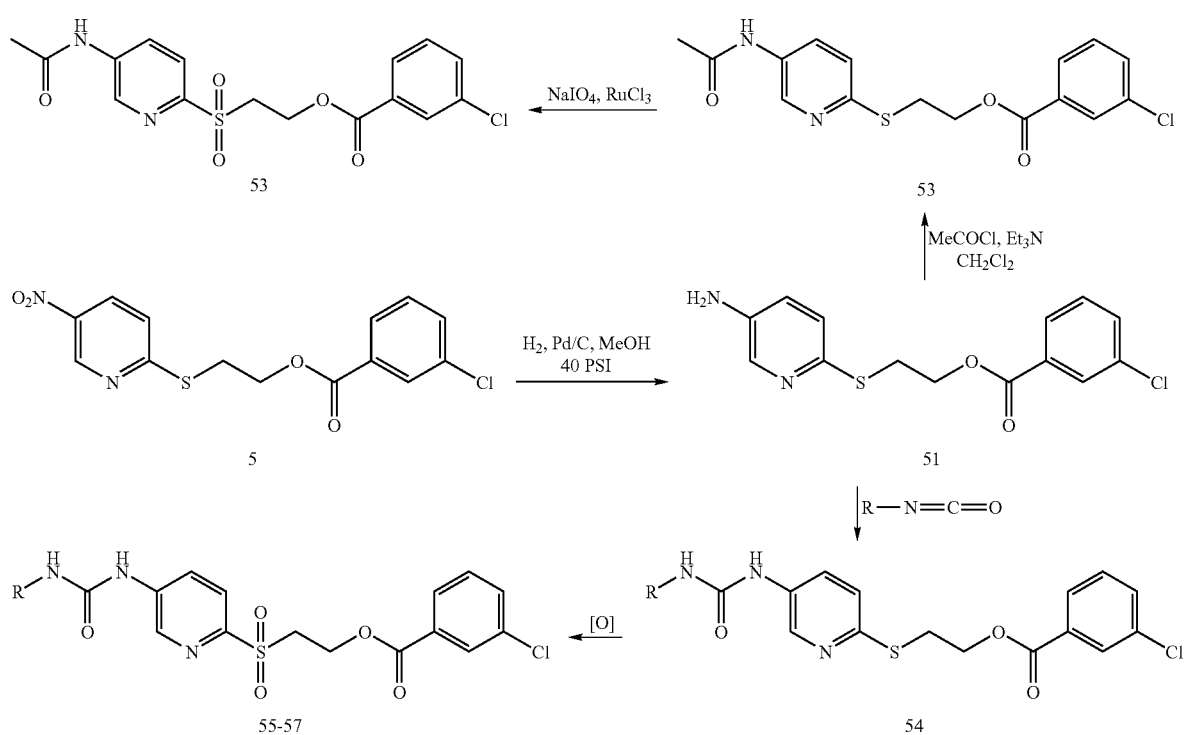

2-[(5-Acetylamino-2-pyridinyl)thio]ethyl-3-chlorobenzoate (52): A mixture of 2-[(5-nitro-2-pyridinyl)thio]ethyl 3-chlorobenzoate (5) (0.24 g, 0.71 mmol) and 10% Pd/C (0.10 g) in toluene or methanol was agitated under a hydrogen atmosphere (40 PSI) for 1 h. The reaction mixture was filtered through Celite® and concentrated to give 2-[(5-amino-2-pyridinyl)thio]ethyl-3-chlorobenzoate (51), LCMS: purity: 99%; MS (m/e): 309 (MH+), which was used without further purification. Acetyl chloride (4.6 μL, 0.064 mmol) was added to a room temperature solution of 2-[(5-amino-2-pyridinyl)thio]ethyl-3-chlorobenzoate (51) (18.9 mg, 0.061 mmol) and triethylamine (18 μL, 0.13 mmol) in anhydrous dichloromethane (1.0 mL), After 16 h, the reaction mixture was diluted with dichloromethane and washed with 1N HCl and brine and then dried over anhydrous MgSO4. Purification by silica gel chromatography provided 2-[(5-acetylamino-2-pyridinyl)thio]ethyl-3-chlorobenzoate (52), LCMS: purity: 99%; MS (m/e): 351 (MH+).

2-[(5-Acetylamino-2-pyridinyl)sulfonyl]ethyl-3-chlorobenzoate (53): The oxidation of 2-[(5-acetylamino-2-pyridinyl)thio]ethyl-3-chlorobenzoate (52) to obtain 2-[(5-acetylamino-2-pyridinyl)sulfonyl]ethyl-3-chlorobenzoate (53) was accomplished in a manner analogous to the procedure outlined in Scheme 1. LCMS: purity: 99%; MS (m/e): 383 (MH+).

55

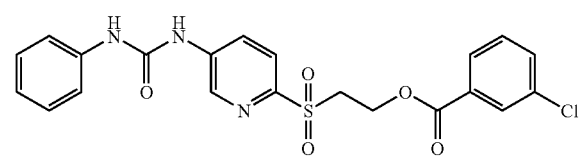

2-[(5-{Phenylureido}-2-pyridinyl)sulfonyl]ethyl-3-chlorobenzoate (55): The reaction of 2-[(5-amino-2-pyridinyl)thio]ethyl-3-chlorobenzoate (51) with phenyl isocyante followed by oxidation as per outlined in Scheme-1 and 5 gave 2-[(5-{phenylureido}-2-pyridinly)sulfonyl]ethyl-3-chlorobenzoate (55). LCMS: purity: 96%; MS (m/e): 461 (MH+).

56

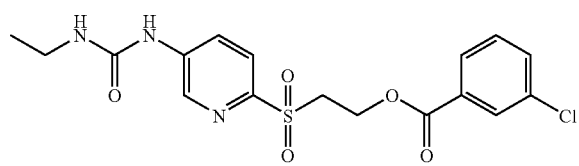

2-[(5-{Ethylureido}-2-pyridinyl)sulfonyl]ethyl-3-chlorobenzoate (56): The reaction of 2-[(5-amino-2-pyridinyl)thio]ethyl-3-chlorobenzoate (51) with ethyl isocyante followed by oxidation as per outlined in Scheme-1 and 5 gave 2-[(5-{ethylureido}-2-pyridinyl)sulfonyl]ethyl-3-chlorobenzoate (56). LCMS: purity: 96%; MS (m/e): 413 (MH+).

57

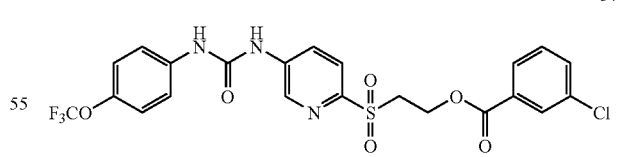

2-[(5-{4-Trifluoromethoxyphenylureido}-2-pyridinyl)sulfonyl]ethyl-3-chlorobenzoate (57: The reaction of 2-[(5-amino-2-pyridinyl)thio]ethyl-3-chlorobenzoate (51) with 4-trifluoromethoxyphenyl isocyante followed by oxidation as per outlined in Scheme-1 and 5 gave 2-[(5-{4-trifluoromethoxyphenylureido}-2-pyridinyl)sulfonyl]ethyl-3-chlorobenzoate (57). LCMS: purity: 98%; MS (m/e): 545 (MH+).

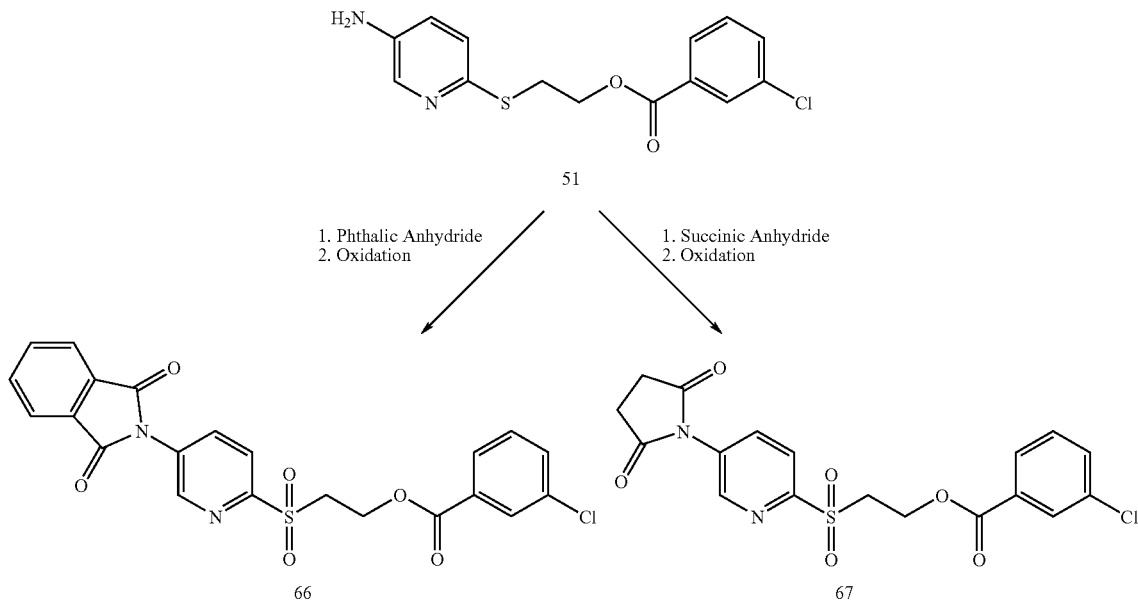

Scheme 6

[(5-{1,3-Dihydro-1,3-dioxo-2H-isoindol-2-yl}-2-pyridinyl)sulfonyl]ethyl 3-chlorobenzoate (66): The reaction of 2-[(5-amino-2-pyridinyl)thio]ethyl 3-chlorobenzoate (51) with phthalic anhydride followed by oxidation (as per Scheme-1) gave [(5-{1,3-dihydro-1,3-dioxo-2H-isoindol-2-yl}-2-pyridinyl)sulfonyl]ethyl 3-chlorobenzoate (66). LCMS: purity: 99%; MS (m/e): 471 (M+).

[(5-{2,5-Dioxotetrahydro-1H-pyrrol-1-yl}-2-pyridinyl)sulfonyl]ethyl 3-chlorobenzoate (67): The reaction of 2-[(5-amino-2-pyridinyl)thio]ethyl 3-chlorobenzoate (51) with succinic anhydride followed by oxidation (as per Scheme-1) gave [(5-{2,5-dioxotetrahydro-1H-pyrrol-1-yl}-2-pyridinyl)sulfonyl]ethyl 3-chlorobenzoate (67). LCMS: purity: 99%; MS (m/e): 423 (MH+).

7.2 The Pyridine Compounds of the Invention Inhibit FcεRI Receptor-Mediated Degranulation The ability of the substituted pyrinde compounds of the invention to inhibit IgE-induced degranulation was demonstrated in a variety of cellular assays with cultured human mast cells (CHMC) and/or mouse bone marrow derived cells (BMMC). Inhibition of degranulation was measured at both low and high cell density by quantifying the release of the granule specific factors tryptase, histamine and hexosaminidase. Inhibition of release and/or synthesis of lipid mediators was assessed by measuring the release of leukotriene LTC4 and inhibition of release and/or synthesis of cytokines was monitored by quantifying TNF-α, IL-6 and IL-13. Tryptase and hexosaminidase were quantified using fluorogenic substrates as described in their respective examples. Histamine, TNFα, IL-6, IL-13 and LTC4 were quantified using the following commercial ELISA kits: histamine (Immunotech #2015, Beckman Coulter), TNFα (Biosource #KHC3011), IL-6 (Biosource #KMC0061), IL-13 (Biosource #KHC0132) and LTC4 (Cayman Chemical #520211). The protocols of the various assays are provided below.

7.2.1 Culturing of Human Mast and Basophil Cells

Human mast and basophil cells were cultured from CD34-negative progenitor cells as described below (see also the methods described in copending U.S. application Ser. No. 10/053,355, filed Nov. 8, 2001, the disclosure of which is incorporated herein by reference).

7.2.2 Preparation of STEMPRO-34 Complete Medium

To prepare STEMPRO-34 complete medium ("CM"), 250 mL STEMPRO-34™ serum free medium ("SFM"; Gibco-BRL, Catalog No. 10640) was added to a filter flask. To this was added 13 mL STEMPRO-34 Nutrient Supplement ("NS"; GibcoBRL, Catalog No. 10641) (prepared as described in more detail, below). The NS container was rinsed with approximately 10 mL SFM and the rinse added to the filter flask. Following addition of 5 mL L-glutamine (200 mM; Mediatech, Catalog No. MT 25-005-CI and 5 mL 100× penicillin/streptomycin ("pen-strep"; HyClone, Catalog No. SV30010), the volume was brought to 500 mL with SFM and the solution was filtered.

The most variable aspect of preparing the CM is the method by which the NS is thawed and mixed prior to addition to the SFM. The NS should be thawed in a 37° C. water bath and swirled, not vortexed or shaken, until it is completely in solution. While swirling, take note whether there are any lipids that are not yet in solution. If lipids are present and the NS is not uniform in appearance, return it to the water bath and repeat the swirling process until it is uniform in appearance. Sometimes this component goes into solution immediately, sometimes after a couple of swirling cycles, and sometimes not at all. If, after a couple of hours, the NS is still not in solution, discard it and thaw a fresh unit. NS that appears non-uniform after thaw should not be used.

7.2.3 Expansion of CD34+ Cells

A starting population of CD34-positive (CD34+) cells of relatively small number (1-5×10$^6$ cells) was expanded to a relatively large number of CD34-negative progenitor cells (about 2-4×10$^9$ cells) using the culture media and methods described below. The CD34+ cells (from a single donor) were obtained from Allcells (Berkeley, Calif.). Because there is a degree of variation in the quality and number of CD34+ cells that Allcells typically provides, the newly delivered cells were transferred to a 15 mL conical tube and brought up to 10 mL in CM prior to use.

On day 0, a cell count was performed on the viable (phase-bright) cells and the cells were spun at 1200 rpm to pellet. The cells were resuspended to a density of 275,000 cells/mL with CM containing 200 ng/mL recombinant human Stem Cell Factor ("SCF"; Peprotech, Catalog No. 300-07) and 20 ng/mL human flt-3 ligand (Peprotech, Catalog No. 300-19) ("CM/SCF/flt-3 medium"). On about day 4 or 5, the density of the culture was checked by performing a cell count and the culture was diluted to a density of 275,000 cells/mL with fresh CM/SCF/flt-3 medium. On about day 7, the culture was transferred to a sterile tube and a cell count was performed. The cells were spun at 1200 rpm and resuspended to a density of 275,000 cells/mL with fresh CM/SCF/flt-3 medium.

This cycle was repeated, starting from day 0, a total of 3-5 times over the expansion period.

When the culture is large and being maintained in multiple flasks and is to be resuspended, the contents of all of the flasks are combined into a single container prior to performing a cell count. This ensures that an accurate cell count is achieved and provides for a degree of uniformity of treatment for the entire population. Each flask is checked separately for contamination under the microscope prior to combining to prevent contamination of the entire population.

Between days 17-24, the culture can begin to go into decline (i.e., approximately 5-10% of the total number of cells die) and fail to expand as rapidly as before. The cells are then monitored on a daily basis during this time, as complete failure of the culture can take place in as little as 24 hours. Once the decline has begun, the cells are counted, spun down at 850 rpm for 15 minutes, and resuspended at a density of 350,000 cells/mL in CM/SCF/flt-3 medium to induce one or two more divisions out of the culture. The cells are monitored daily to avoid failure of the culture.

When greater than 15% cell death is evident in the progenitor cell culture and some debris is present in the culture, the CD34-negative progenitor cells are ready to be differentiated.

7.2.4 Differentiation of CD34-Negative Progenitor Cells into Mucosal Mast Cells A second phase is performed to convert the expanded CD34-negative progenitor cells into differentiated mucosal mast cells. These mucosal cultured human mast cells ("CHMC") are derived from CD34+ cells isolated from umbilical cord blood and treated to form a proliferated population of CD34-negative progenitor cells, as described above. To produce the CD43-negative progenitor cells, the resuspension cycle for the culture was the same as that described above, except that the culture was seeded at a density of 425,000 cells/mL and 15% additional media was added on about day four or five without performing a cell count. Also, the cytokine composition of the medium was modified such that it contained SCF (200 ng/mL) and recombinant human IL-6 (200 ng/mL; Peprotech, Catalog No. 200-06 reconstituted to 100 ug/mL in sterile 10 mM acetic acid) ("CM/SCF/IL-6 medium").

Phases I and II together span approximately 5 weeks. Some death and debris in the culture is evident during weeks 1-3 and there is a period during weeks 2-5 during which a small percentage of the culture is no longer in suspension, but is instead attached to the surface of the culture vessel.

As during Phase I, when the culture is to be resuspended on day seven of each cycle, the contents of all flasks are combined into a single container prior to performing a cell count to ensure uniformity of the entire population. Each flask is checked separately for contamination under the microscope prior to combining to prevent contamination of the entire population.

When the flasks are combined, approximately 75% of the volume is transferred to the communal container, leaving behind about 10 mL or so in the flask. The flask containing the remaining volume was rapped sharply and laterally to dislodge the attached cells. The rapping was repeated at a right angle to the first rap to completely dislodge the cells.

The flask was leaned at a 45 degree angle for a couple of minutes before the remaining volume was transferred to the counting vessel. The cells were spun at 950 rpm for 15 min prior to seeding at 35-50 mL per flask (at a density of 425,000 cells/mL).

7.2.5 Differentiation of CD34-Negative Progenitor Cells into Connective Tissue-Type Mast Cells A proliferated population of CD34-negative progenitor cells is prepared as above and treated to form a tryptase/chymase positive (connective tissue) phenotype. The methods are performed as described above for mucosal mast cells, but with the substitution of IL-4 for IL-6 in the culture medium. The cells obtained are typical of connective tissue mast cells.

7.2.6 Differentiation of CD34-Negative Progenitor Cells into Basophil Cells

A proliferated population of CD34-negative progenitor cells is prepared as described in Section 7.2.1.3, above, and used to form a proliferated population of basophil cells. The CD34-negative cells are treated as described for mucosal mast cells, but with the substitution of IL-3 (at 20-50 ng/mL) for IL-6 in the culture medium.

7.2.7 CHMC Low Cell Density IgE Activation: Tryptase and LTC4 Assays

To duplicate 96-well U-bottom plates (Costar 3799) add 65 ul of compound dilutions or control samples that have been prepared in MT [137 mM NaCl, 2.7 mM KCl, 1.8 mM $CaCl_2$, 1.0 mM $MgCl_2$, 5.6 mM Glucose, 20 mM Hepes (pH 7.4), 0.1% Bovine Serum Albumin, (Sigma A4503)] containing 2% MeOH and 1% DMSO. Pellet CHMC cells (980 rpm, 10 min) and resuspend in pre-warmed MT. Add 65 ul of cells to each 96-well plate. Depending on the degranulation activity for each particular CHMC donor, load 1000-1500 cells/well. Mix four times followed by a 1 hr incubation at 37° C. During the 1 hr incubation, prepare 6× anti-IgE solution [rabbit anti-human IgE (1 mg/ml, Bethyl Laboratories A80-109A) diluted 1:167 in MT buffer]. Stimulate cells by adding 25 ul of 6× anti-IgE solution to the appropriate plates. Add 25 ul MT to un-stimulated control wells. Mix twice following addition of the anti-IgE. Incubate at 37° C. for 30 minutes. During the 30 minute incubation, dilute the 20 mM tryptase substrate stock solution [(Z-Ala-Lys-Arg-AMC 2TFA; Enzyme Systems Products, #AMC-246)] 1:2000 in tryptase assay buffer [0.1 M Hepes (pH 7.5), 10% w/v Glycerol, 10 uM Heparin (Sigma H-4898) 0.01% $NaN_3$]. Spin plates at 1000 rpm for 10 min to pellet cells. Transfer 25 ul of supernatant to a 96-well black bottom plate and add 100 ul of freshly diluted tryptase substrate solution to each well. Incubate plates at room temperature for 30 min. Read the optical density of the plates at 355 nm/460 nm on a spectrophotometric plate reader.

Leukotriene C4 (LTC4) is also quantified using an ELISA kit on appropriately diluted supernatant samples (determined empirically for each donor cell population so that the sample measurement falls within the standard curve) following the supplier's instructions.

7.3 CHMC High Cell Density IgE Activation: Degranulation (Tryptase, Histamine), Leukotriene (LTC4), and Cytokine (TNFalpha, IL-13) Assays Cultured human mast cells (CHMC) are sensitized for 5 days with IL-4 (20 ng/ml), SCF (200 ng/ml), IL-6 (200 ng/ml), and Human IgE (CP 1035K from Cortx Biochem, 100-500 ng/ml depending on generation) in CM medium.

After sensitizing, cells are counted, pelleted (1000 rpm, 5-10 minutes), and resuspended at $1-2\times10^6$ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× anti-IgE. Mix wells with the cells and allow plates to incubate at 37° C. (5% $CO_2$) for one hour. After 1 hour incubation, pellet cells (10 minutes, 1000 RPM) and collect 200 ul per well of the supernatant, being careful not to disturb pellet. Place the supernatant plate on ice. During the 7-hour step (see next) perform tryptase assay on supernatant that had been diluted 1:500. Resuspend cell pellet in 240 ul of CM media containing 0.5% DMSO and corresponding concentration of compound. Incubate CHMC cells for 7 hours at 37° C. (5% $CO_2$). After incubation, pellet cells (1000 RPM, 10 minutes) and collect 225 ul per well and place in −80° C. until ready to perform ELISAS. ELISAS are performed on appropriately diluted samples (determined empirically for each donor cell population so that the sample measurement falls within the standard curve) following the supplier's instructions.

Results. The results of low density CHMC assays are provided in Tables 1 and 2. In Tables 1 and 2, all reported values are $IC_{50}$s (in μM). Most compounds tested had $IC_{50}$s of less than 10 μM, with many exhibiting $IC_{50}$s in the sub-micromolar range. In Tables 1 and 2, all reported values are $IC_{50}$s (in μM). A value of "−" indicates an $IC_{50}>10$ μM, with no measurable activity at a 10 μM concentration. Most compounds tested had $IC_{50}$s of less than 10 μM, with many exhibiting $IC_{50}$s in the sub-micromolar range. A value of "+" indicates an $IC_{50}<10$ μM. Of the compounds tested, BMMC values are comparable to those noted for the CHMC results.

7.4 The Pyridine Compounds of the Invention Selectively Inhibit the Upstream IgE Receptor Cascade To confirm that many of the pyridine compounds of the invention exert their inhibitory activity by blocking or inhibiting the early IgE receptor signal transduction cascade, several of the compounds were tested in cellular assays for ionomycin-induced degranulation, as described below.

7.5 CHMC Low Cell Density Ionomycin Activation: Tryptase Assay

Assays for ionomycin-induced mast cell degranulation were carried out as described for the CHMC Low Density IgE Activation assays, supra, with the exception that during the 1 hour incubation, 6× ionomycin solution [5 mM ionomycin (Sigma I-0634) in MeOH (stock) diluted 1:416.7 in MT buffer (2 μM final)] was prepared and cells were stimulated by adding 25 μl of the 6× ionomycin solution to the appropriate plates.

Results. The results of the ionomycin-induced degranulation assays, reported as $IC_{50}$ values (in μM) are provided in TABLES 1 and 2. Of the active compounds tested (i.e., those that inhibit IgE-induced degranulation), the vast majority do not inhibit ionomycin-induced degranulation, confirming that these active compounds selectively inhibit the early (or upstream) IgE receptor signal transduction cascade. In TABLES 1 and 2, all reported values are $IC_{50}$s (in μM). A value of "−" indicates an $IC_{50}>10$ μM, with no measurable activity at a 10 μM concentration. A value of "+" indicates an $IC_{50}<10$ μM.

TABLE 1

| Compound | IgE/Iono | p | X | A |
|---|---|---|---|---|
| 5 | −/− | 0 | O | 3-chlorophenyl |
| 100 | +/− | 0 | O | 2-chlorophenyl |
| 101 | −/− | 0 | O | 4-chlorophenyl |
| 102 | −/− | 0 | O | 3-trifluoromethylphenyl |
| 103 | +/− | 0 | O | 2-trifluoromethylphenyl |
| 6 | +/+ | 2 | O | 2-chlorophenyl |
| 9 | +/+ | 2 | O | 4-chlorophenyl |
| 11 | +/+ | 2 | O | 3-trifluoromethylphenyl |
| 12 | +/+ | 2 | O | 2-trifluoromethylphenyl |
| 13 | +/+ | 2 | O | phenyl |
| 14 | +/+ | 2 | O | 2-fluorophenyl |
| 15 | +/+ | 2 | O | 3-fluorophenyl |
| 16 | +/+ | 2 | O | 4-fluorophenyl |
| 17 | +/+ | 2 | O | methyl |
| 18 | +/+ | 2 | O | ethyl |
| 19 | +/+ | 2 | O | 3-trifluoromethoxyphenyl |
| 50 | +/+ | 1 | O | 3-chlorophenyl |
| 40 | +/+ | 2 | NH | methyl |
| 42 | +/+ | 2 | NH | 3-chlorophenyl |
| 41 | +/+ | 2 | NH | t-butoxy |

TABLE 2

| Compound | IgE/Iono | Y | p | X |
|---|---|---|---|---|
| 53 | | acetamido-t-butyl | 2 | O |
| 55 | −/− | phenyl-NH-C(O)-NH-t-butyl | 2 | O |
| 56 | −/− | ethyl-NH-C(O)-NH-t-butyl | 2 | O |
| 57 | +/+ | 4-F$_3$CO-phenyl-NH-C(O)-NH-t-butyl | 2 | O |
| 66 | +/+ | phthalimido-t-butyl | 2 | O |

TABLE 2-continued

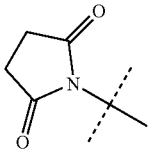

| Compound | IgE/Iono | Y | p | X |
|---|---|---|---|---|
| 67 | −/− | 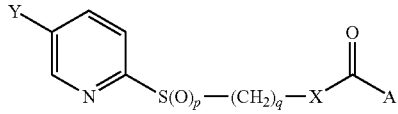 | 2 | O |
| 21 | +/+ | trifluoromethyl | 2 | O |

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

What is claimed is:

1. A compound according to structural formula (I):

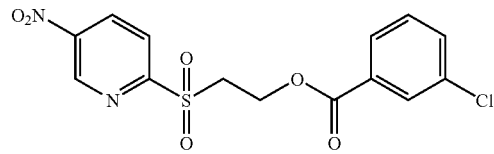

(I)

including a pharmaceutically acceptable salt and/or N-oxide thereof, wherein:

Y is selected from the group consisting of $NR_3+$, $SR_2+$, $NH_3+$, $NO_2$, $SO_2R$, $SO_2Aryl$, COOH, OAryl, COOR, —C(O)R, SH, SR, OH, —C≡CR, Aryl, —CH=$CR_2$, $NH_2$, $NHR^1$, and $NR^1R^2$;

p is 0, 1 or 2;

q is an integer between 1 and 6, inclusive;

each R individually is a hydrogen, alkyl, or an aryl;

each $R^1$ and $R^2$ individually is an alkyl or aryl;

X is NH or $NR^3$;

$R^3$ is an alkyl or aryl; and

A is selected from alkyl, aryl, aryl substituted with a halo, lower haloalkyl, or lower haloalkoxy, and alkoxy, with the proviso that the compound is not included.

2. The compound of claim 1 in which Y is —$NO_2$.

3. The compound of claim 1 in which p is 2.

4. The compound of claim 1 in which q is 2.

5. The compound of claim 1 in which A is selected from the group consisting of methyl, ethyl and t-butoxy.

6. The compound of claim 1 in which A is a phenyl or a phenyl substituted with a halo, lower haloalkyl, or lower haloalkoxy.

7. The compound of claim 6 in which the substituted phenyl is monosubstituted.

8. The compound of claim 7 in which the substituted phenyl is monosubstituted with a substituent selected from the group consisting of halo, lower haloalkyl, and lower haloalkoxy.

9. The compound of claim 1 which is selected from the group consisting of compounds 40, 42 and 41.

10. A composition comprising a pharmaceutically acceptable vehicle and a compound according to claim 1.

* * * * *